US012029516B2

(12) United States Patent
Soto et al.

(10) Patent No.: US 12,029,516 B2
(45) Date of Patent: Jul. 9, 2024

(54) ROBOTIC MANIPULATOR COMPRISING ISOLATION MECHANISM FOR FORCE/TORQUE SENSOR

(71) Applicant: MAKO Surgical Corp., Weston, FL (US)

(72) Inventors: Victor Soto, Coral Gables, FL (US); David Gene Bowling, Los Ranchos De Albuquerque, NM (US); Ezra Johnson, Reeds Spring, MO (US); Nicholas Joseph LaBarbera, Tamarac, FL (US)

(73) Assignee: MAKO Surgical Corp., Weston, FL (US)

( * ) Notice: Subject to any disclaimer, the term of this patent is extended or adjusted under 35 U.S.C. 154(b) by 334 days.

(21) Appl. No.: 17/668,063

(22) Filed: Feb. 9, 2022

(65) Prior Publication Data

US 2022/0273378 A1    Sep. 1, 2022

Related U.S. Application Data

(60) Provisional application No. 63/148,381, filed on Feb. 11, 2021.

(51) Int. Cl.
*A61B 34/37*    (2016.01)
*A61B 90/00*    (2016.01)

(52) U.S. Cl.
CPC ........ *A61B 34/37* (2016.02); *A61B 2090/066* (2016.02); *A61B 2560/0266* (2013.01)

(58) Field of Classification Search
CPC .............. A61B 34/37; A61B 2090/066; A61B 2560/0266
See application file for complete search history.

(56) References Cited

U.S. PATENT DOCUMENTS

| 5,449,153 A | 9/1995 | Catalano et al. |
| 5,577,414 A | 11/1996 | Ogawa et al. |

(Continued)

FOREIGN PATENT DOCUMENTS

| JP | 2004116442 A | 4/2004 |
| JP | 2009088210 A | 4/2009 |

(Continued)

OTHER PUBLICATIONS

International Search Report for Application No. PCT/US2022/015763 dated Jul. 18, 2022, 3 pages.

(Continued)

*Primary Examiner* — Jaime Figueroa
*Assistant Examiner* — Mohamad O El Sayah
(74) *Attorney, Agent, or Firm* — Howard & Howard Attorneys PLLC

(57) ABSTRACT

A robotic manipulator includes an arm including at least one joint driven by a transmission comprising an output, an isolation mechanism coupled to the output of the transmission, and a force/torque sensor coupled to the isolation mechanism. The force/torque sensor includes a body, which includes a stationary part and a movable part coupled to and being movable relative to the stationary part. The force/torque sensor also includes one or more sensing elements configured to sense forces and torques applied to the movable part. The isolation mechanism is configured to deform in response to forces induced by the transmission to mechanically isolate the force/torque sensor from forces induced by the transmission.

20 Claims, 23 Drawing Sheets

(56) References Cited

U.S. PATENT DOCUMENTS

| | | | |
|---|---|---|---|
| 5,789,890 A | 8/1998 | Genov et al. | |
| 6,325,566 B1 | 12/2001 | Devine | |
| 6,478,486 B1 | 11/2002 | Ando | |
| 6,752,547 B2 | 6/2004 | Britcher et al. | |
| 6,968,755 B2 | 11/2005 | Kobayashi et al. | |
| 7,117,754 B2 | 10/2006 | Neely et al. | |
| 7,665,373 B2 | 2/2010 | Sakers et al. | |
| 8,161,827 B2 | 4/2012 | Kato et al. | |
| 8,176,809 B2 | 5/2012 | Ihrke et al. | |
| 8,291,775 B2 | 10/2012 | Nagasaka et al. | |
| 8,291,788 B2 | 10/2012 | Ihrke et al. | |
| 8,412,371 B2 | 4/2013 | Komatsu | |
| 8,435,309 B2 | 5/2013 | Gilbert et al. | |
| 8,443,693 B2 | 5/2013 | Ihrke et al. | |
| 8,443,694 B2 | 5/2013 | Ihrke et al. | |
| 8,449,624 B2 | 5/2013 | Evans et al. | |
| 8,512,199 B2 | 8/2013 | Rosmarin | |
| 8,706,429 B2 | 4/2014 | Nakajima | |
| 8,876,094 B1 | 11/2014 | Ridgeway et al. | |
| 9,008,757 B2 | 4/2015 | Wu | |
| 9,066,740 B2 | 6/2015 | Carlson et al. | |
| 9,086,101 B2 | 7/2015 | Zhu et al. | |
| 9,095,984 B2 | 8/2015 | Miyazaki | |
| 9,114,028 B2 | 8/2015 | Langenfeld et al. | |
| 9,119,655 B2 | 9/2015 | Bowling et al. | |
| 9,234,561 B2 | 1/2016 | Laurens | |
| 9,239,100 B1 | 1/2016 | Weber et al. | |
| 9,242,375 B2 | 1/2016 | Orita et al. | |
| 9,333,039 B2 | 5/2016 | Kuchenbecker et al. | |
| 9,381,099 B2 | 7/2016 | Perry et al. | |
| 9,393,131 B2 | 7/2016 | Evans et al. | |
| 9,409,298 B2 | 8/2016 | Rosmarin et al. | |
| 9,513,176 B1 | 12/2016 | Weber et al. | |
| 9,523,626 B2 | 12/2016 | Zusman | |
| 9,556,920 B1 | 1/2017 | Knoll et al. | |
| 9,656,396 B2 | 5/2017 | Miyazaki | |
| 9,739,674 B2 | 8/2017 | Malackowski et al. | |
| 9,772,240 B2 | 9/2017 | Hulse et al. | |
| 9,796,082 B2 | 10/2017 | Choset et al. | |
| 9,796,087 B2 | 10/2017 | Osada et al. | |
| 9,987,094 B2 | 6/2018 | Allen et al. | |
| 9,993,309 B2 | 6/2018 | Bowling | |
| 9,995,357 B2 | 6/2018 | Miyazaki | |
| 10,145,747 B1* | 12/2018 | Lin | A61B 90/06 |
| 10,245,725 B2 | 4/2019 | Ogawara | |
| 10,299,869 B2 | 5/2019 | Allen et al. | |
| 10,299,941 B2 | 5/2019 | Langenfeld et al. | |
| 10,335,959 B2 | 7/2019 | Ogata | |
| 10,434,665 B2 | 10/2019 | Nakayama | |
| 10,444,098 B2 | 10/2019 | Nakayama | |
| 10,486,309 B2 | 11/2019 | Ishikawa et al. | |
| 10,626,944 B2 | 4/2020 | Liao et al. | |
| 2006/0107761 A1 | 5/2006 | Meyer et al. | |
| 2007/0156157 A1 | 7/2007 | Nahum et al. | |
| 2008/0075561 A1 | 3/2008 | Takemura et al. | |
| 2009/0091070 A1 | 4/2009 | Mueller et al. | |
| 2010/0268031 A1* | 10/2010 | Koyama | A61B 1/0051 600/146 |
| 2012/0205931 A1 | 8/2012 | Ohta | |
| 2012/0296472 A1 | 11/2012 | Nagai | |
| 2012/0330429 A1 | 12/2012 | Axelson, Jr. et al. | |
| 2014/0158492 A1 | 6/2014 | Roby | |
| 2014/0276949 A1 | 9/2014 | Staunton et al. | |
| 2015/0051732 A1 | 2/2015 | Grygorowicz et al. | |
| 2016/0102724 A1 | 4/2016 | Potter et al. | |
| 2016/0114483 A1 | 4/2016 | Ishikawa et al. | |
| 2016/0202134 A1 | 7/2016 | Malackowski et al. | |
| 2017/0285625 A1 | 10/2017 | Sato et al. | |
| 2018/0071035 A1 | 3/2018 | Marshall et al. | |
| 2018/0281182 A1 | 10/2018 | Yokota et al. | |
| 2018/0291995 A1 | 10/2018 | Hayashibara et al. | |
| 2019/0061168 A1 | 2/2019 | Wang et al. | |
| 2019/0160658 A1 | 5/2019 | Hutter et al. | |
| 2019/0201111 A1 | 7/2019 | Shelton, IV et al. | |
| 2019/0255709 A1 | 8/2019 | Nagaki et al. | |
| 2019/0299421 A1 | 10/2019 | Kim et al. | |
| 2019/0307580 A1 | 10/2019 | Langenfeld et al. | |
| 2020/0054401 A1* | 2/2020 | Yu | B25J 9/1633 |
| 2020/0170724 A1 | 6/2020 | Flatt et al. | |
| 2020/0281673 A1* | 9/2020 | Suzuki | A61B 17/29 |
| 2020/0367986 A1* | 11/2020 | Nichogi | A61B 34/37 |
| 2020/0384643 A1* | 12/2020 | Hariri | B25J 9/1653 |
| 2021/0131891 A1* | 5/2021 | Hoshino | B25J 13/085 |
| 2021/0267700 A1* | 9/2021 | Hares | B25J 9/1697 |
| 2021/0298850 A1* | 9/2021 | Huang | A61B 34/30 |
| 2022/0000568 A1* | 1/2022 | Hufford | A61B 34/32 |

FOREIGN PATENT DOCUMENTS

| | | |
|---|---|---|
| JP | 2010060132 A | 3/2010 |
| JP | 2014136612 A | 7/2014 |
| RU | 2650320 C2 | 4/2018 |
| WO | 2010142318 A1 | 12/2010 |
| WO | 2020092256 A1 | 5/2020 |

OTHER PUBLICATIONS

English language abstract and machine-assisted English translation for JP 2004-116442 A extracted from espacenet.com database on Feb. 10, 2022, 8 pages.

English language abstract and machine-assisted English translation for JP 2009-088210 A extracted from espacenet.com database on Feb. 10, 2022, 25 pages.

English language abstract for JP 2010-060132 A extracted from espacenet.com database on Feb. 10, 2022, 1 page.

English language abstract and machine-assisted English translation for JP 2014-136612 A extracted from espacenet.com database on Feb. 10, 2022, 12 pages.

English language abstract and machine-assisted English translation for RU 2650320 C2 extracted from espacenet.com database on Feb. 10, 2022, 5 pages.

* cited by examiner

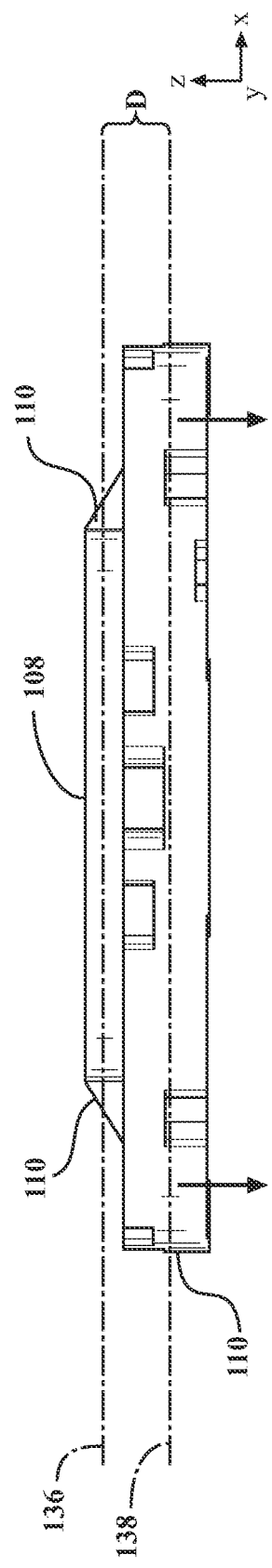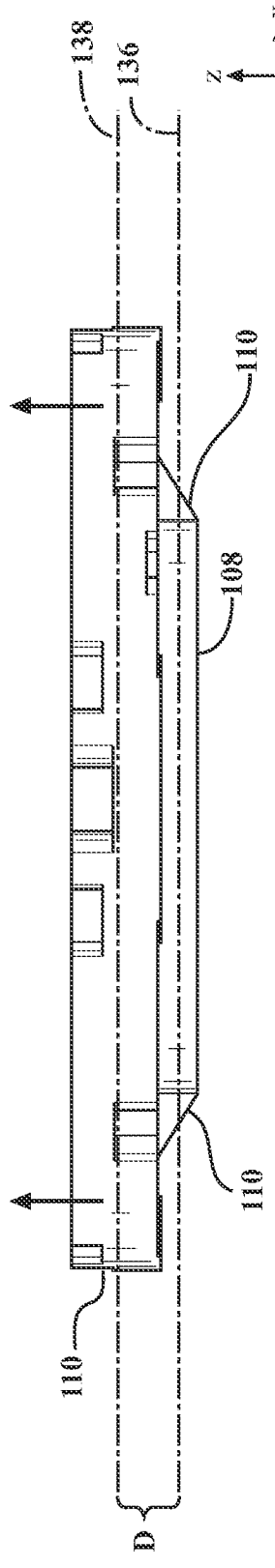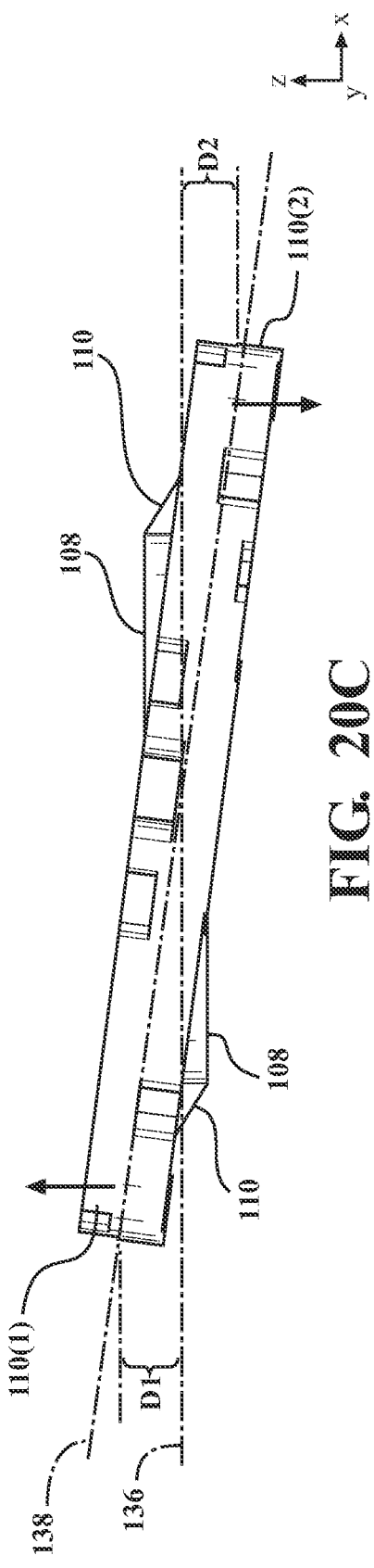

ROBOTIC MANIPULATOR COMPRISING ISOLATION MECHANISM FOR FORCE/TORQUE SENSOR

CROSS-REFERENCE TO RELATED APPLICATIONS

The present application claims priority to and all the benefits of U.S. Provisional Patent Application No. 63/148,381 filed Feb. 11, 2021, the disclosure of which is hereby incorporated by reference in its entirety.

TECHNICAL FIELD

The present disclosure relates generally to a mechanism for isolating a force/torque sensor from forces induced by joint transmission.

BACKGROUND

Robotic surgical systems perform surgical procedures at surgical sites. Robotic surgical systems typically include a manipulator comprising a plurality of links and joints and an end effector coupled to the manipulator. A surgical tool is coupled to, or part of, the end effector and is designed to remove tissue at the surgical site.

Admittance-controlled robotic surgical systems utilize inverse-kinematics to provide a commanded position for the surgical tool based on a solution to a complex system of equations. One variable to the inverse-kinematic solution can be external forces/torques experienced by or applied to the end effector or surgical tool by a user or the surgical environment. These external forces/torques can be sensed by a force/torque sensor located adjacent to the surgical tool and/or end effector. The robotic surgical system accounts for the forces/torques sensed by the force/torque sensor when determining the commanded position of the surgical tool. When the force is applied by a user, the robotic surgical system can position the surgical tool to emulate the user's intentions. To accurately position the surgical tool in these scenarios, it is desirable for the force/torque sensor to accurately sense such external forces/torques.

However, it has been observed that the force/torque sensor is susceptible to sensing undesired forces induced by one or more transmission(s) of the joint(s) of the robotic surgical system. The undesired forces induced by the transmission(s) arise internal to the manipulator, not from external forces. Because transmission operation typically occurs during joint movement of the manipulator, such undesired forces can be induced at the same time external forces/torques are experienced by or applied to the end effector or surgical tool. The undesired forces can be picked up by the force/torque sensor and interfere with the force/torque sensor's ability to accurately sense external forces. In turn, this condition can adversely influence the manipulator's ability to accurately position the surgical tool because the system accounts for the undesired forces in the inverse-kinematic solution.

There is a need in the art for systems and methods to address at least these challenges.

SUMMARY

This Summary introduces a selection of concepts in a simplified form that are further described in the Detailed Description below. This Summary is not intended to limit the scope of the claimed subject matter nor identify key features or essential features of the claimed subject matter.

According to a first aspect, a robotic manipulator is provided. The robotic manipulator includes an arm including at least one joint driven by a transmission comprising an output, an isolation mechanism coupled to the output of the transmission, and a force/torque sensor coupled to the isolation mechanism. The force/torque sensor includes a body, which includes a stationary part and a movable part coupled to and being movable relative to the stationary part. The force/torque sensor also includes one or more sensing elements configured to sense forces and torques applied to the movable part. The isolation mechanism is configured to deform in response to forces induced by the transmission to mechanically isolate the force/torque sensor from forces induced by the transmission.

According to a second aspect, a robotic manipulator is provided. The robotic manipulator includes an arm including at least one joint driven by a transmission comprising an output, an isolation mechanism coupled to the output of the transmission, and a force/torque sensor coupled to the isolation mechanism. The isolation mechanism includes a body, which includes at least one elastic part and at least one rigid part. The force/torque sensor includes a body, which includes a stationary part and a movable part coupled to and being movable relative to the stationary part. The force/torque sensor also includes one or more sensing elements configured to sense forces and torques applied to the movable part. The at least one elastic part of the isolation mechanism is configured to deform in response to forces induced by the transmission to mechanically isolate the force/torque sensor from forces induced by the transmission.

According to a third aspect, an isolation mechanism is provided that includes a body comprising at least one elastic part and at least one rigid part. The elastic part is configured to deform in response to forces induced by a transmission to mechanically isolate a force/torque sensor from forces induced by the transmission.

According to a fourth aspect, an isolated sensor assembly is provided. The assembly comprises a force/torque sensor that includes a body, which includes a stationary part and a movable part coupled to and being movable relative to the stationary part. The force/torque sensor also includes one or more sensing elements configured to sense forces and torques applied to the movable part. The force/torque sensor is coupled to an isolation mechanism. The isolation mechanism is configured to couple to an output of a transmission. The isolation mechanism includes a body comprising at least one elastic part and at least one rigid part. The elastic part is configured to deform in response to forces induced by the transmission to mechanically isolate the force/torque sensor from forces induced by the transmission.

According to a fifth aspect, a transmission assembly is provided. The transmission assembly comprises a transmission comprising an output and isolation mechanism coupled to the output of the transmission. The isolation mechanism includes a body comprising at least one elastic part and at least one rigid part. The elastic part is configured to deform in response to forces induced by a transmission to mechanically isolate forces induced by the transmission.

According to a sixth aspect, a force/torque sensor having a configuration specifically shown in FIGS. 2, 6, 10 and 18 is provided.

Any of the above aspects can be utilized individually, or in combination.

Any of the above aspects can be utilized with any of the following implementations.

In one implementation, the at least one elastic part is coupled to the output of the transmission. In one implementation, the at least one rigid part is coupled to one of the stationary part and the movable part of the force/torque sensor. In one implementation, the at least one rigid part is coupled to the output of the transmission. In one implementation, the at least one elastic part is coupled to one of the stationary part and the movable part of the force/torque sensor.

In one implementation, the body of the isolation mechanism comprises a first rigid part and a second rigid part. In one implementation, the at least one elastic part is disposed between the first and second rigid parts. In one implementation, the first rigid part is coupled to the output of the transmission. In one implementation, the second rigid part is coupled to the movable part of the force/torque sensor.

In one implementation, an end effector includes or is configured to receive a surgical instrument that includes an energy applicator. In one implementation, the end effector comprises an attachment mount. In one implementation, the robotic manipulator comprises a distal link assembly comprising a mounting interface configured to detachably receive the attachment mount of the end effector.

In one implementation, the force/torque sensor is disposed between the isolation mechanism and the mounting interface of the distal link assembly. In one implementation, the movable part of the force/torque sensor is rigidly attached to the mounting interface of the distal link assembly. In one implementation, the force/torque sensor is configured to sense forces and/or torques applied to or experienced by the end effector or surgical instrument.

In one implementation, the at least one elastic part of the isolation mechanism is configured to deform in response to forces induced by the transmission to mechanically isolate the movable part of the force/torque sensor from forces induced by the transmission. In one implementation, the force/torque sensor senses forces and/or torques applied to or experienced by the end effector or surgical instrument substantially free from interference from forces induced by the transmission.

In one implementation, one or more controllers are configured to control the at least one joint of the arm to move the energy applicator to a commanded position. In one implementation, the one or more controllers are configured to determine the commanded position based, in part, on the forces and/or torques applied to or experienced by the end effector or surgical instrument sensed by the force/torque sensor.

In one implementation, the first rigid part is disposed concentrically about the at least one elastic part. In one implementation, the at least one elastic part is disposed concentrically around the second rigid part.

In one implementation, the at least one elastic part comprises a plurality of elastic segments extending between the first and second rigid parts.

In one implementation, the body of the isolation mechanism comprises a first surface and a second surface opposite the first surface. In one implementation, a geometrical configuration of each elastic segment is defined in part by at least two hollows formed adjacent to each elastic segment. In one implementation, the at least two hollows are defined through the body between the first surface and the second surface.

In one implementation, the body of the isolation mechanism comprises a planar configuration and a central axis. In one implementation, the body of the isolation mechanism comprises an opening formed about the central axis. In one implementation, the at least one elastic part is configured to deform within a plane perpendicular to the central axis. In one implementation, the at least one elastic part is configured to deform within the plane in a direction transverse to the central axis. In one implementation, the at least one elastic part is configured to deform within the plane in a rotational direction about the central axis. In one implementation, the at least one elastic part is configured to deform beyond the plane in an axial direction along the central axis.

In one implementation, the body of the force/torque sensor comprises: a planar configuration and an opening aligned with the opening of the isolation mechanism. In one implementation, a plurality of deformable members connects the movable part and the stationary part. In one implementation, the one or more sensing elements are disposed on the deformable members.

In one implementation, the at least one rigid part of the isolation mechanism is monolithically formed with the output of the transmission. In one implementation, the at least one rigid part of the isolation mechanism is separately attached to the output of the transmission.

In one implementation, the isolation mechanism comprises at least a first body and a second body, each comprising at least one elastic part and at least one rigid part. In one implementation, the at least one elastic part or the least one rigid part of the first body is coupled to the at least one elastic part or the at least rigid part of the second body. In one implementation, the first and second bodies are stacked axially.

In one implementation, the transmission is a strain wave gear transmission. In one implementation, the transmission is a planetary gear set and/or a cycloidal drive, or any other type of low-backlash or zero-backlash transmission.

In one implementation, the isolation mechanism is absent any electrical or electronic components. In one implementation, the isolation mechanism is purely a mechanical component. In one implementation, the isolation mechanism may comprise one or more sensors for sensing forces induced by the transmission.

Any of the above implementations can be combined in part, or in whole, with any of the aspects.

DESCRIPTION OF THE DRAWINGS

Advantages of the present disclosure will be readily appreciated as the same becomes better understood by reference to the following detailed description when considered in connection with the accompanying drawings.

FIGS. 20A-20C are side views of one implementation of the isolation mechanism where an elastic part of the isolation mechanism deforms in an axial direction.

DETAILED DESCRIPTION

I. Overview of Surgical System

A. Example Robotic System

Figure 1:
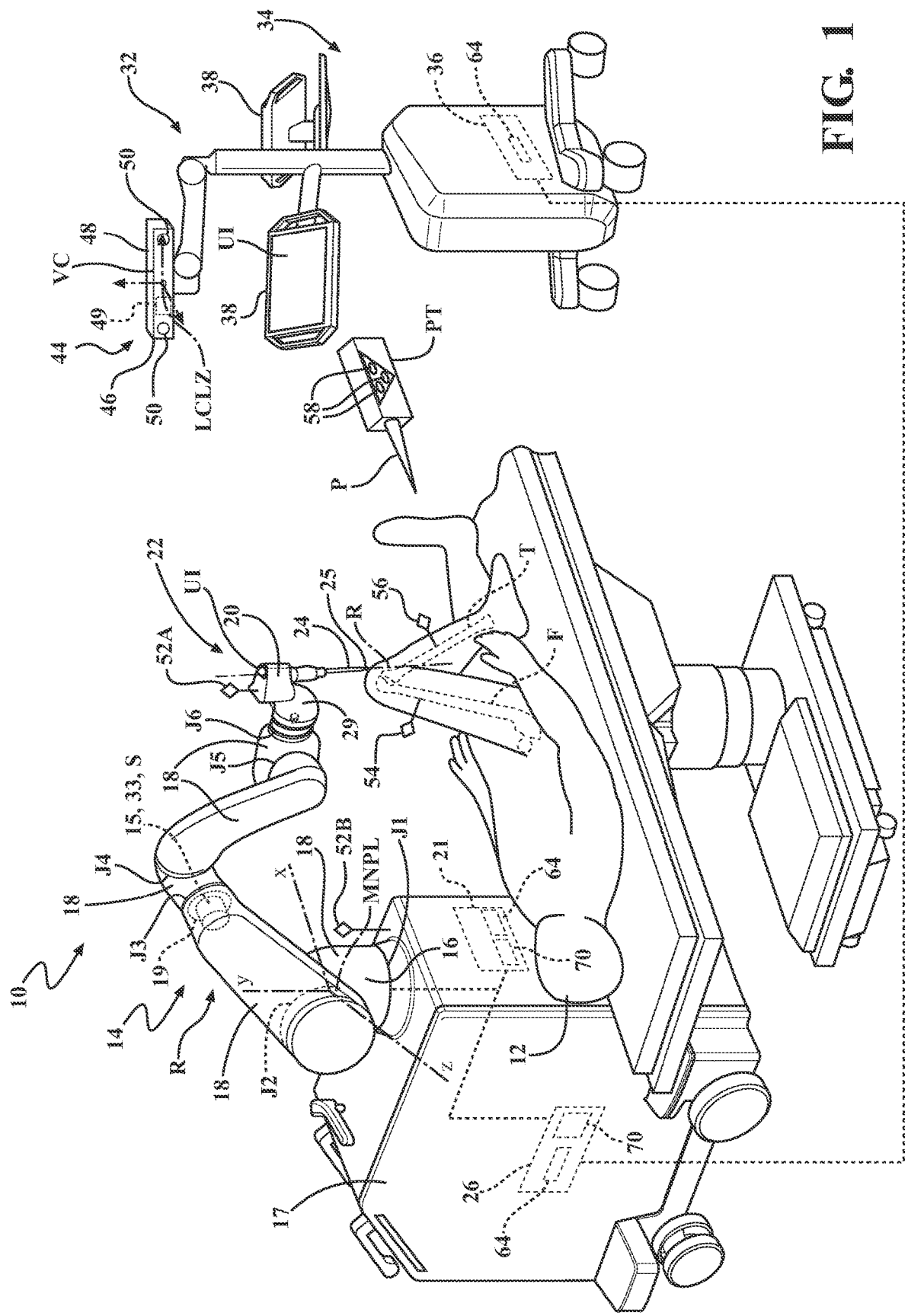
FIG. 1 is a perspective view of a robotic surgical system according to one example.

Referring to FIG. 1, a surgical system 10 is illustrated. The system 10 is useful for treating a surgical site or anatomical volume (A) of a patient 12, such as treating bone or soft tissue. In FIG. 1, the system 10 is a robotic surgical system and the patient 12 is undergoing a surgical procedure. The anatomy in FIG. 1 includes a femur F and a tibia T of the patient 12. The surgical procedure may involve tissue removal or other forms of treatment. Treatment may include cutting, coagulating, lesioning the tissue, other in-situ tissue treatments, or the like. In some examples, the surgical procedure involves partial or total knee or hip replacement surgery, shoulder replacement surgery, spine surgery, or ankle surgery. In some examples, the system 10 is designed to cut away material to be replaced by surgical implants, such as hip and knee implants, including unicompartmental, bicompartmental, multicompartmental, or total knee implants. Some of these types of implants are shown in U.S. Patent Application Publication No. 2012/0330429, entitled "Prosthetic Implant and Method of Implantation," the disclosure of which is hereby incorporated by reference. The system 10 and techniques disclosed herein may be used to perform other procedures, surgical or non-surgical, or may be used in industrial applications or other applications where robotic systems are utilized.

In one example, the system 10 includes a manipulator 14. The manipulator 14 has a base 16 and a plurality of links 18. A manipulator cart 17 supports the manipulator 14 such that the manipulator 14 is fixed to the manipulator cart 17. The links 18 collectively form one or more robotic arms R of the manipulator 14. The manipulator 14 may have a serial arm configuration (as shown in FIG. 1), a parallel arm configuration, or any other suitable manipulator configuration. In other examples, more than one manipulator 14 may be utilized in a multiple arm configuration.

In the example shown in FIG. 1, the manipulator 14 comprises a plurality of joints J and a plurality of joint encoders 19 located at the joints J for determining position data of the joints J. For simplicity, only one joint encoder 19 is illustrated in FIG. 1, although other joint encoders 19 may be similarly illustrated. The manipulator 14 according to one example has six joints J1-J6 implementing at least six-degrees of freedom (DOF) for the manipulator 14. However, the manipulator 14 may have any number of degrees of freedom and may have any suitable number of joints J and may have redundant joints.

The manipulator 14 need not require joint encoders 19 but may alternatively, or additionally, utilize motor encoders present on motors 15 coupled to any number of joints J. Also, the manipulator 14 need not require rotary joints, but may alternatively, or additionally, utilize one or more prismatic or linear joints. Any suitable combination of joint types is contemplated.

Figure 2:
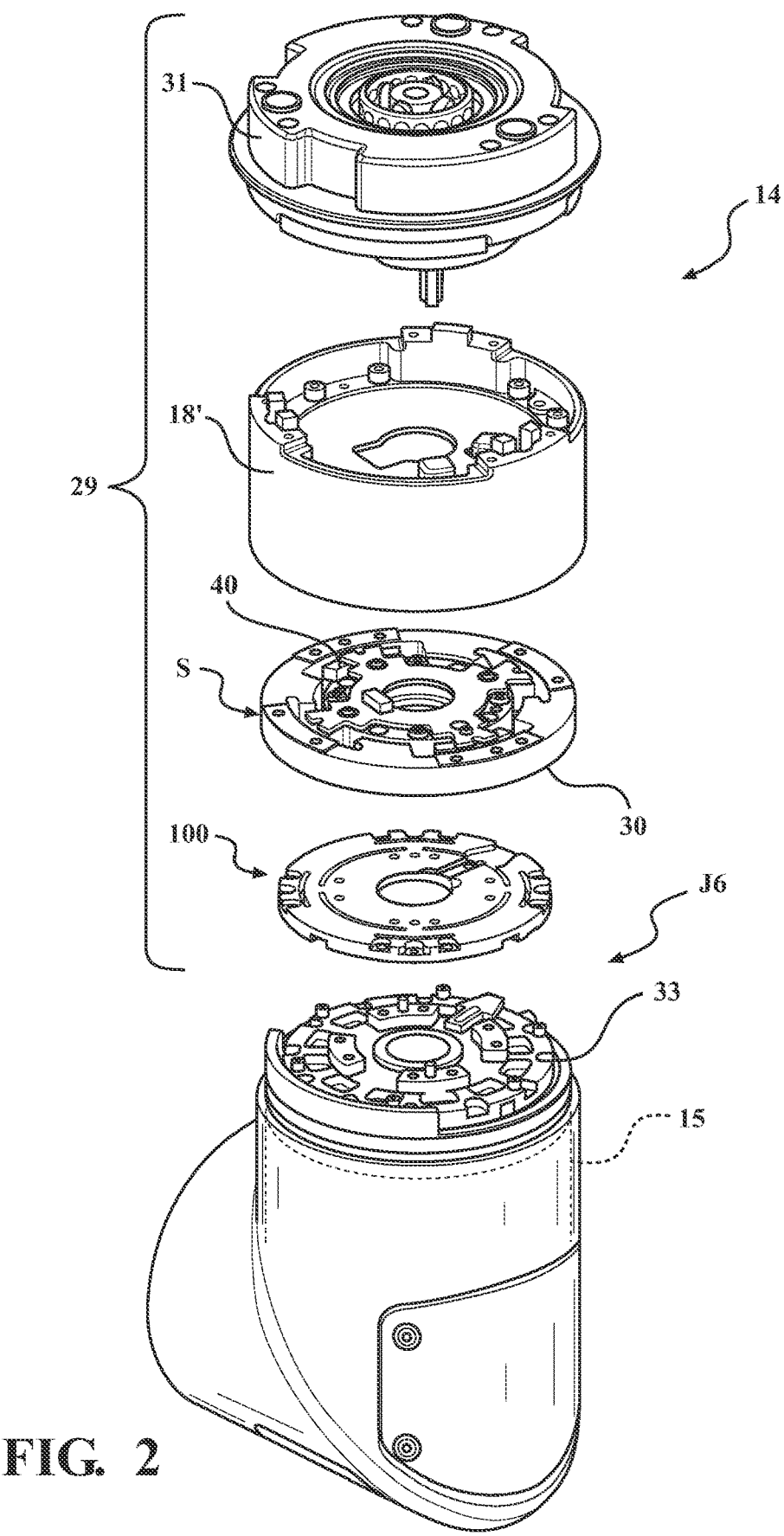
FIG. 2 is an exploded view of a distal link assembly and joint J6 of the robotic surgical system of FIG. 1, according to one implementation.

Referring to FIG. 2, the manipulator 14 may include a motor 15 at a joint J. The manipulator 14 also includes a transmission 33 coupled to the motor 15 and, more specifically, the output of the motor 15. The transmission 33 transfers motion of the motor 15 to articulation of the link 18 coupled to the respective joint J and often is used for gear-reduction to balance capabilities of the motor 15 with load requirements. FIG. 2 shows the distal-most joint J6 of the manipulator 14 as well as a link 18' coupled to the joint J6, the link 18' being a part of a distal link assembly 29 configured to receive an end effector 22. The motor 15 and transmission 33 can be located at each of the joints J or any number of other joints J.

Figure 3A:
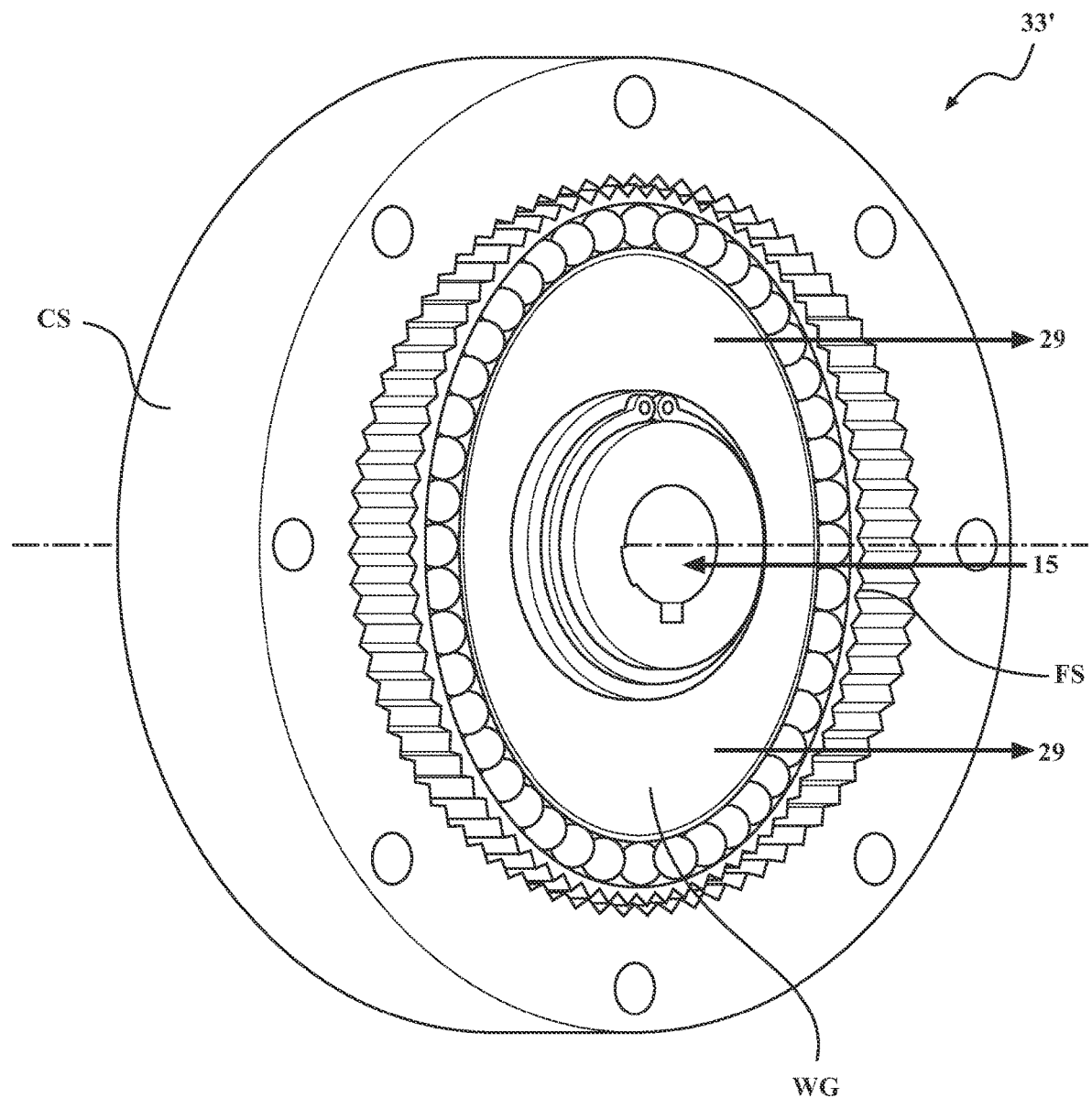
FIG. 3A is a perspective view of one example of a strain wave gear transmission of the robotic surgical system of FIG. 1.
Figure 3B:
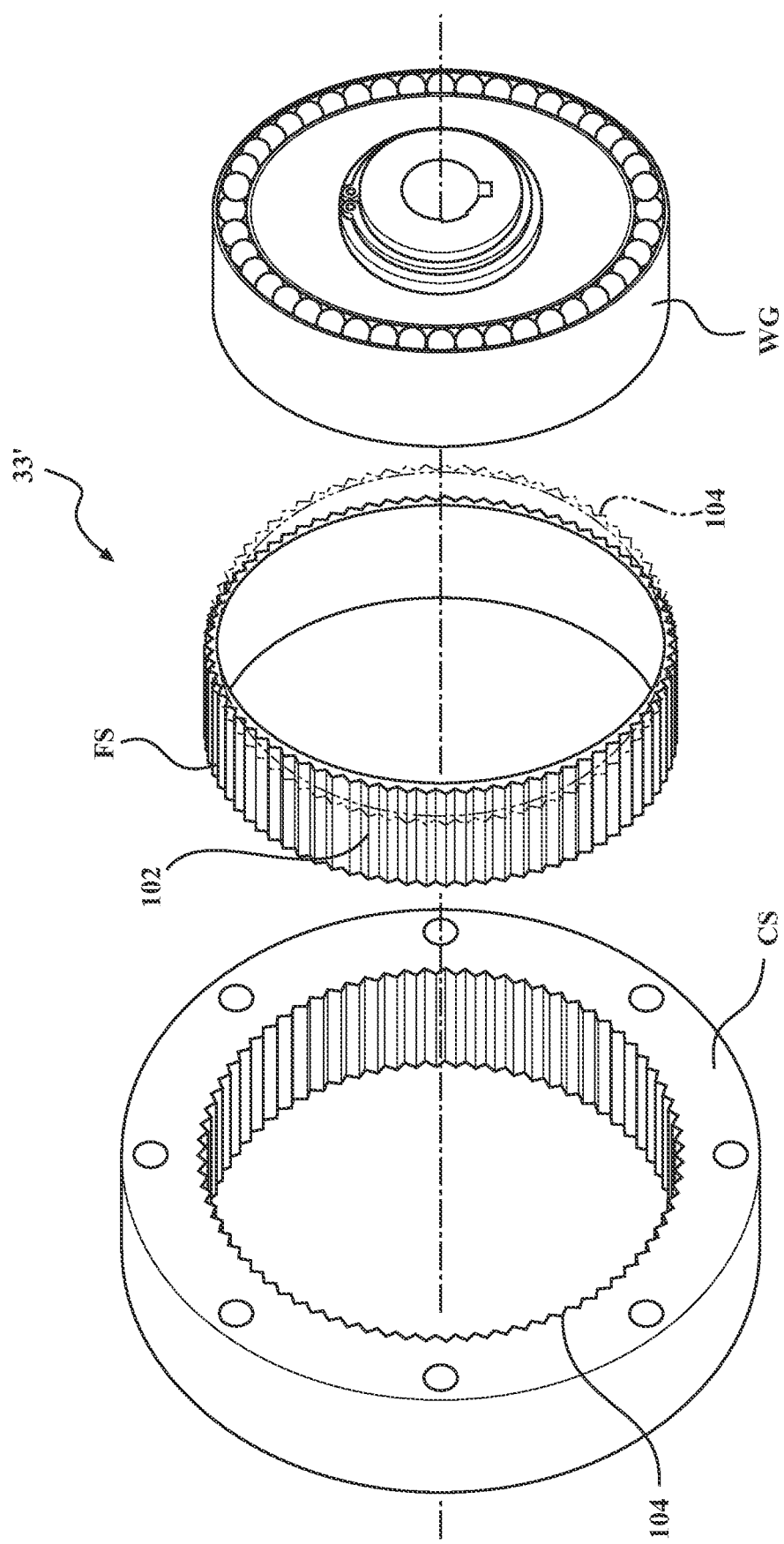
FIG. 3B is an exploded view of the strain wave gear transmission of FIG. 3A.

In one example, the transmission 33 may be a strain wave gear transmission 33' shown in one implementation of FIGS. 3A and 3B. The strain wave gear transmission 33' may include a wave generator WG, a flex spline FS, and a circular spline CS for housing the flex spline FS and the wave generator WG. The flex spline FS includes teeth 102 and the circular spline CS includes teeth 104, as shown in FIG. 3B. The number of teeth 104 of the circular spline CS is greater than the number of teeth 102 of the flex spline FS, allowing for gear-reduction to occur when the wave generator WG drives the flex spline FS and the flex spline FS rotates within the circular spline CS. The output of the motor 15 may be coupled to the wave generator WG and the flex spline FS may be coupled to the distal link assembly 29 such that the strain wave gear transmission 33' transfers motion of the motor 15 to articulation of the link 18'. One example of a strain wave gear transmission that can be utilized with the techniques described herein can be like that described in U.S. Pat. No. 6,968,755, entitled "Lightweight Bearing and Wave Gear Drive," the disclosure of which is hereby incorporated by reference in its entirety.

In other instances, the transmission 33 may be any suitable transmission for driving the joints J. For example, the transmission 33 may include a planetary gear set and/or a cycloidal drive, or any other type of low-backlash or zero-backlash transmission.

As shown in FIG. 1, the base 16 of the manipulator 14 is generally a portion of the manipulator 14 that provides a fixed reference coordinate system for other components of the manipulator 14 or the system 10 in general. Generally, the origin of a manipulator coordinate system MNPL is defined at the fixed reference of the base 16. The base 16 may be defined with respect to any suitable portion of the manipulator 14, such as one or more of the links 18. Alternatively, or additionally, the base 16 may be defined with respect to the manipulator cart 17, such as where the manipulator 14 is physically attached to the manipulator cart 17. In one example, the base 16 is defined at an intersection of the axes of joints J1 and J2. Thus, although joints J1 and J2 are moving components in reality, the intersection of the axes of joints J1 and J2 can be a virtual fixed reference pose, which provides both a fixed position and orientation reference and which does not move relative to the manipulator 14 and/or manipulator cart 17. In other examples, the manipulator 14 can be a hand-held manipulator where the base 16 is a base portion of a tool (e.g., a portion held free-hand by the user) and the tool tip is movable relative to the base portion. The base portion has a reference coordinate system that is tracked, and the tool tip has a tool tip coordinate system that is computed relative to the reference coordinate system (e.g., via motor and/or joint encoders and forward kinematic calculations). Movement of the tool tip can be controlled to follow the path since its pose relative to the path can be determined.

The manipulator 14 and/or manipulator cart 17 house a manipulator controller 26, or other type of control unit. The manipulator controller 26 may comprise one or more computers, or any other suitable form of controller that directs the motion of the manipulator 14. The manipulator controller 26 may have a central processing unit (CPU) and/or other processors, memory (not shown), and storage (not shown). The manipulator controller 26 is loaded with software as described below. The processors could include one or more processors to control operation of the manipulator 14. The processors can be any type of microprocessor, multi-processor, and/or multi-core processing system. The manipulator controller 26 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor. The manipulator 14 may also comprise a user interface UI with one or more displays and/or input devices (e.g., push buttons, keyboard, mouse, microphone (voice-activation), gesture control devices, touchscreens, etc.).

As shown in FIG. 1, a tool 20 couples to the manipulator 14 and is movable relative to the base 16 to interact with the anatomy in certain modes. The tool 20 is a physical and surgical tool and is or forms part of an end effector 22 supported by the manipulator 14 in certain embodiments. The tool 20 may be grasped by the user. One possible arrangement of the manipulator 14 and the tool 20 is described in U.S. Pat. No. 9,119,655, entitled "Surgical Manipulator Capable of Controlling a Surgical Instrument in Multiple Modes," the disclosure of which is hereby incorporated by reference. The manipulator 14 and the tool 20 may be arranged in alternative configurations. The tool 20 can be like that shown in U.S. Patent Application Publication No. 2014/0276949, filed on Mar. 15, 2014, entitled "End Effector of a Surgical Robotic Manipulator," hereby incorporated by reference.

The tool 20 may be mounted to the manipulator 14 via a link 18 of the plurality of links 18. In one implementation, referring to FIGS. 4A and 4B, the tool 20 comprises an attachment mount 27 and the manipulator 14, shown as robotic arm R, comprises a distal link assembly 29 including a mounting interface 31 configured to detachably receive the attachment mount 27 of the end effector 22. In order to facilitate releasable attachment of the tool 20 to the robotic arm R, a tensioner 35 attached (e.g., to the end effector 22 mounting interface 31 or attachment mount 27) is movable between a first position 35F and a second position 35S. The mounting interface 31 includes a coupler C and kinematic couplers KC. As shown, the coupler C of the mounting interface 31 is configured to releasably secure to the distal link assembly 29 and to releasably receive the attachment mount 27 when the tensioner 35 is in the first position 35F. The kinematic couplers KC of the mounting interface 31 are configured to engage the attachment mount 27 and the distal link assembly 29 and are arranged to provide a kinematic coupling between the attachment mount 27 and the distal link assembly 29 to constrain six degrees of freedom of movement between the surgical components when the tensioner 35 is in the second position 35S. In some instances, the tool 20 may be mounted to the manipulator 14 with a sterile barrier assembly, as described in U.S. Patent Application Publication No. 2020/0170724A1, filed on Dec. 4, 2019, entitled "Mounting System With Sterile Barrier Assembly For Use In Coupling Surgical Components," hereby incorporated by reference.

Figure 4B:
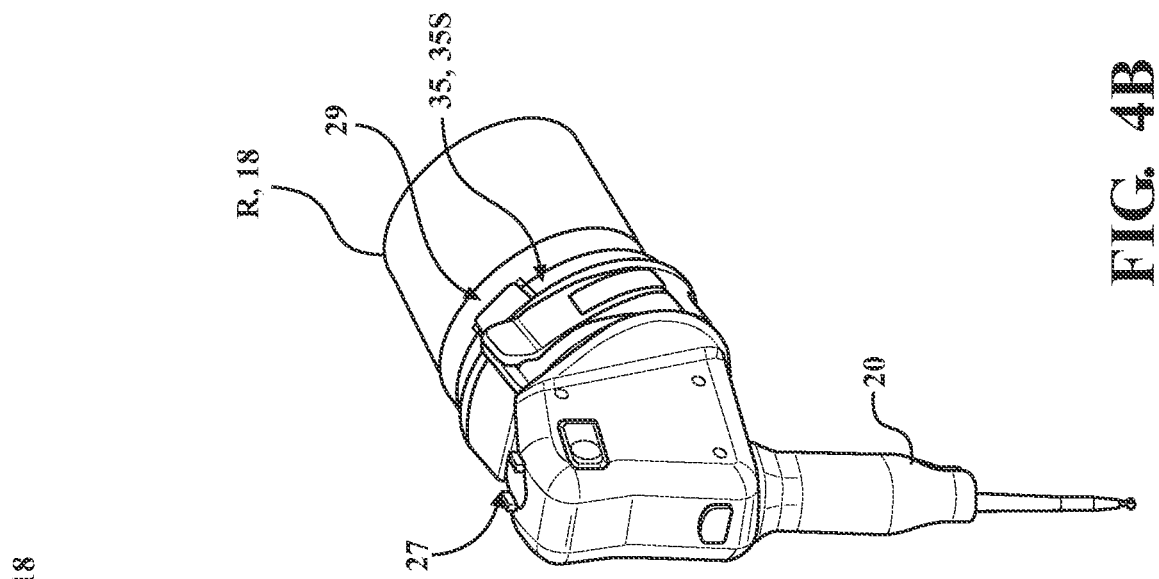
FIG. 4B is a perspective view of the mounting system of FIG. 4A shown with first and second mounting portions arranged in a loaded configuration.
Figure 4A:
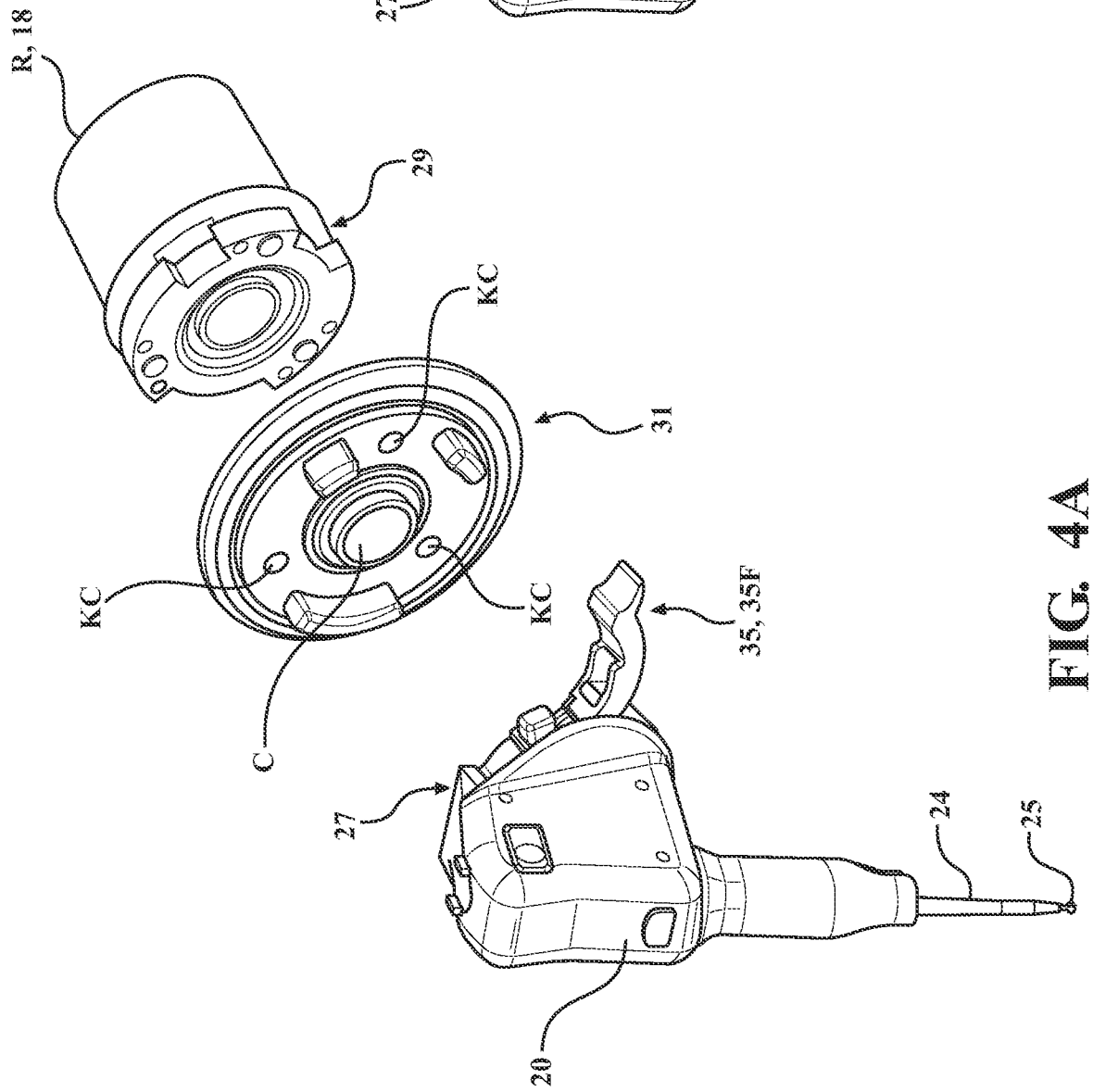
FIG. 4A is an assembly perspective view of an example of a mounting system that can be utilized by the robotic surgical system.

Also shown in FIGS. 4A and 4B, the tool 20 includes an energy applicator 24 designed to contact and remove the tissue of the patient 12 at the surgical site. In one example, the energy applicator 24 is a bur 25. The bur 25 may be substantially spherical and comprise a spherical center, radius (r) and diameter. Alternatively, the energy applicator 24 may be a drill bit, a saw blade, an ultrasonic vibrating tip, or the like. The tool 20 and/or energy applicator 24 may comprise any geometric feature, e.g., perimeter, circumference, radius, diameter, width, length, volume, area, surface/plane, range of motion envelope (along any one or more axes), etc. The geometric feature may be considered to determine how to locate the tool 20 relative to the tissue at the surgical site to perform the desired treatment. In some of the embodiments described herein, a spherical bur having a tool center point (TCP) will be described for convenience and ease of illustration, but is not intended to limit the tool 20 to any particular form.

Figure 5:
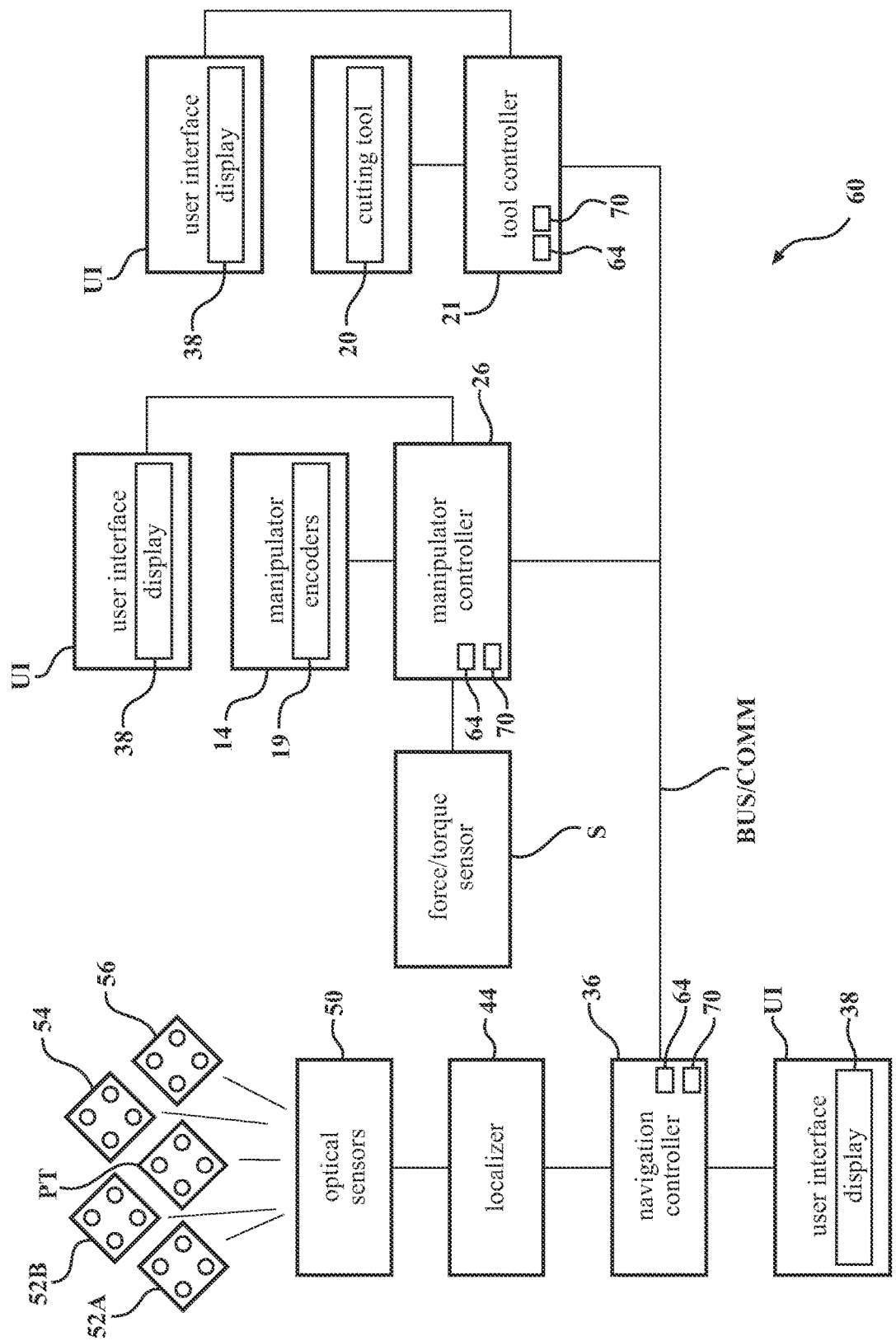
FIG. 5 is a block diagram of an example control system for controlling the robotic surgical system.

Referring to FIG. 5, the tool 20 may comprise a tool controller 21 to control operation of the tool 20, such as to control power to the tool (e.g., to a rotary motor of the tool 20), control movement of the tool 20, control irrigation/aspiration of the tool 20, and/or the like. The tool controller 21 may be in communication with the manipulator controller 26 or other components. The tool 20 may also comprise a user interface UI with one or more displays and/or input devices (e.g., push buttons, keyboard, mouse, microphone (voice-activation), gesture control devices, touchscreens, etc.). The manipulator controller 26 controls a state (position and/or orientation) of the tool 20 (e.g., the tool center point (TCP)) with respect to a coordinate system, such as the manipulator coordinate system MNPL. The manipulator controller 26 can control (linear or angular) velocity, acceleration, or other derivatives of motion of the tool 20.

In one example, the TCP is a predetermined reference point defined at the energy applicator 24. The TCP has a known, or able to be calculated (i.e., not necessarily static), pose relative to other coordinate systems. The geometry of the energy applicator 24 is known in or defined relative to a TCP coordinate system. The TCP may be located at the spherical center of the bur 25 of the tool 20 such that one point is tracked. The TCP may be defined in various ways depending on the configuration of the energy applicator 24. The manipulator 14 could employ the joint/motor encoders, or any other non-encoder position sensing method, to enable a pose of the TCP to be determined. The manipulator 14 may use joint measurements to determine TCP pose and/or could employ techniques to measure TCP pose directly. The control of the tool 20 is not limited to a center point. For example, any suitable primitives, meshes, etc., can be used to represent the tool 20.

B. Optional Navigation System

The system 10 may further include a navigation system 32. One example of the navigation system 32 is described in U.S. Pat. No. 9,008,757, filed on Sep. 24, 2013, entitled "Navigation System Including Optical and Non-Optical Sensors," hereby incorporated by reference. The navigation system 32 tracks movement of various objects. Such objects include, for example, the manipulator 14, the tool 20 and the anatomy, e.g., femur F and tibia T. The navigation system 32 tracks these objects to gather state information of each object with respect to a (navigation) localizer coordinate system LCLZ. Coordinates in the localizer coordinate system LCLZ may be transformed to the manipulator coordinate system MNPL, and/or vice-versa, using transformations.

The navigation system 32 includes a cart assembly 34 that houses a navigation controller 36, and/or other types of control units. A navigation user interface UI is in operative communication with the navigation controller 36. The navigation user interface includes one or more displays 38. The navigation system 32 is capable of displaying a graphical representation of the relative states of the tracked objects to the user using the one or more displays 38. The navigation user interface UI further comprises one or more input devices to input information into the navigation controller 36 or otherwise to select/control certain aspects of the navigation controller 36. Such input devices include interactive touchscreen displays. The input devices may include any one or more of push buttons, a keyboard, a mouse, a microphone (voice-activation), gesture control devices, and the like.

The navigation system 32 also includes a navigation localizer 44 coupled to the navigation controller 36. In one example, the localizer 44 is an optical localizer and includes a camera unit 46. The camera unit 46 has an outer casing 48 that houses one or more optical sensors 50. The localizer 44 may comprise its own localizer controller 49 and may further comprise a video camera VC.

The navigation system 32 includes one or more trackers. In one example, the trackers include a pointer tracker PT, one or more manipulator trackers 52A, 52B, a first patient tracker 54, and a second patient tracker 56, shown in FIG. 5. In the illustrated example of FIG. 1, the manipulator tracker is firmly attached to the tool 20 (i.e., tracker 52A), the first patient tracker 54 is firmly affixed to the femur F of the patient 12, and the second patient tracker 56 is firmly affixed to the tibia T of the patient 12. In this example, the patient trackers 54, 56 are firmly affixed to sections of bone. The pointer tracker PT is firmly affixed to a pointer P used for registering the anatomy to the localizer coordinate system LCLZ. The manipulator trackers 52A, 52B may be affixed to any suitable component of the manipulator 14 in addition to, or other than, the tool 20, such as the base 16 (i.e., tracker 52B), or any one or more links 18 of the manipulator 14. The trackers 52A, 52B, 54, 56, PT may be fixed to their respective components in any suitable manner. For example, the trackers may be rigidly fixed, flexibly connected (optical fiber), or not physically connected at all (ultrasound), as long as there is a suitable (supplemental) way to determine the relationship (measurement) of that respective tracker to the object that it is associated with.

Any one or more of the trackers may include active markers 58. The active markers 58 may include light emitting diodes (LEDs). Alternatively, the trackers 52A, 52B, 54, 56, PT may have passive markers, such as reflectors, which reflect light emitted from the camera unit 46. Other suitable markers not specifically described herein may be utilized.

The localizer 44 tracks the trackers 52A, 52B, 54, 56, PT to determine a state of each of the trackers 52A, 52B, 54, 56, PT, which corresponds respectively to the state of the object to which it is attached. The localizer 44 may perform known triangulation techniques to determine the states of the trackers 52, 54, 56, PT, and associated objects. The localizer 44 provides the state of the trackers 52A, 52B, 54, 56, PT to the navigation controller 36. In one example, the navigation controller 36 determines and communicates the state the trackers 52A, 52B, 54, 56, PT to the manipulator controller 26. As used herein, the state of an object includes, but is not limited to, data that defines the position and/or orientation of the tracked object or equivalents/derivatives of the position and/or orientation. For example, the state may be a pose of the object, and may include linear velocity data, and/or angular velocity data, and the like.

The navigation controller 36 may comprise one or more computers, or any other suitable form of controller. The navigation controller 36 has a central processing unit (CPU) and/or other processors, memory (not shown), and storage (not shown). The processors can be any type of processor, microprocessor or multi-processor system. The navigation controller 36 is loaded with software. The software, for example, converts the signals received from the localizer 44 into data representative of the position and orientation of the objects being tracked. The navigation controller 36 may additionally, or alternatively, comprise one or more microcontrollers, field programmable gate arrays, systems on a chip, discrete circuitry, and/or other suitable hardware, software, or firmware that is capable of carrying out the functions described herein. The term processor is not intended to limit any implementation to a single processor.

Although one example of the navigation system 32 is shown that employs triangulation techniques to determine object states, the navigation system 32 may have any other suitable configuration for tracking the manipulator 14, tool 20, and/or the patient 12. In another example, the navigation system 32 and/or localizer 44 are ultrasound-based. For example, the navigation system 32 may comprise an ultrasound imaging device coupled to the navigation controller 36. The ultrasound imaging device images any of the aforementioned objects, e.g., the manipulator 14, the tool 20, and/or the patient 12, and generates state signals to the navigation controller 36 based on the ultrasound images. The ultrasound images may be 2-D, 3-D, or a combination of both. The navigation controller 36 may process the images in near real time to determine states of the objects. The ultrasound imaging device may have any suitable configuration and may be different than the camera unit 46 as shown in FIG. 1.

In another example, the navigation system 32 and/or localizer 44 are radio frequency (RF)-based. For example, the navigation system 32 may comprise an RF transceiver coupled to the navigation controller 36. The manipulator 14, the tool 20, and/or the patient 12 may comprise RF emitters or transponders attached thereto. The RF emitters or transponders may be passive or actively energized. The RF transceiver transmits an RF tracking signal and generates state signals to the navigation controller 36 based on RF signals received from the RF emitters. The navigation controller 36 may analyze the received RF signals to associate relative states thereto. The RF signals may be of any suitable frequency. The RF transceiver may be positioned at any suitable location to track the objects using RF signals effectively. Furthermore, the RF emitters or transponders may have any suitable structural configuration that may be much different than the trackers 52A, 52B, 54, 56, PT shown in FIG. 1.

In yet another example, the navigation system 32 and/or localizer 44 are electromagnetically based. For example, the navigation system 32 may comprise an EM transceiver coupled to the navigation controller 36. The manipulator 14, the tool 20, and/or the patient 12 may comprise EM components attached thereto, such as any suitable magnetic tracker, electro-magnetic tracker, inductive tracker, or the like. The trackers may be passive or actively energized. The EM transceiver generates an EM field and generates state signals to the navigation controller 36 based upon EM signals received from the trackers. The navigation controller 36 may analyze the received EM signals to associate relative states thereto. Again, such examples of the navigation system may have structural configurations that are different than the navigation system 32 configuration shown in FIG. 1.

The navigation system 32 may have any other suitable components or structure not specifically recited herein. Furthermore, any of the techniques, methods, and/or components described above with respect to the navigation system 32 shown may be implemented or provided for any of the other examples of the navigation system 32 described herein. For example, the navigation system 32 may utilize solely inertial tracking or any combination of tracking techniques, and may additionally, or alternatively, comprise fiber optic-based tracking, machine-vision tracking, and the like.

C. Control System

Referring to FIG. 5, the system 10 includes a control system 60 that comprises, among other components, the manipulator controller 26, the navigation controller 36 (if applicable), and the tool controller 21. The control system 60 further includes one or more software programs and software modules shown in FIG. 5. The software modules may be part of the program or programs that operate on the manipulator controller 26, navigation controller 36, tool controller 21, or any combination thereof, to process data to assist with control of the system 10. The software programs and/or modules include computer readable instructions stored in non-transitory memory 64 on the manipulator controller 26, navigation controller 36, tool controller 21, or a combination thereof, to be executed by one or more processors 70 of the controllers 21, 26, 36. The memory 64 may be any suitable configuration of memory, such as RAM, non-volatile memory, etc., and may be implemented locally or from a remote database. Additionally, software modules for prompting and/or communicating with the user may form part of the program or programs and may include instructions stored in memory 64 on the manipulator controller 26, navigation controller 36, tool controller 21, or any combination thereof. The user may interact with any of the input devices of the navigation user interface UI or other user interface UI to communicate with the software modules. The user interface software may run on a separate device from the manipulator controller 26, navigation controller 36, and/or tool controller 21.

The control system 60 may comprise any suitable configuration of input, output, and processing devices suitable for carrying out the functions and methods described herein. The control system 60 may comprise the manipulator controller 26, the navigation controller 36, or the tool controller 21, or any combination thereof, or may comprise only one of these controllers. These controllers may communicate via a wired bus or communication network, as shown in FIG. 2, via wireless communication, or otherwise. The control system 60 may also be referred to as a controller. The control system 60 may comprise one or more microcontrollers, field programmable gate arrays, systems on a chip, discrete circuitry, sensors, displays, user interfaces, indicators, and/or other suitable hardware, software, or firmware that is capable of carrying out the functions described herein.

The system 10 may operate in a manual mode, such as described in U.S. Pat. No. 9,119,655, incorporated herein by reference in its entirety. Here, the user manually directs, and the manipulator 14 executes, movement of the tool 20 and its energy applicator 24 at the surgical site. The user physically contacts the tool 20 to apply external force and cause movement of the tool 20 in the manual mode. The system 10 may also operate in a semi-autonomous mode in which the manipulator 14 moves the tool 20 along a milling path (e.g., the active joints J of the manipulator 14 operate to move the tool 20 without necessarily requiring external force/torque on the tool 20 from the user). An example of operation in the semi-autonomous mode is also described in U.S. Pat. No. 9,119,655, incorporated herein by reference. In some embodiments, when the manipulator 14 operates in the semi-autonomous mode, the manipulator 14 is capable of moving the tool 20 free of user assistance. Free of user assistance may mean that a user does not physically contact the tool 20 to move the tool 20. Instead, the user may use some form of remote control to control starting and stopping of movement. For example, the user may hold down a button of the remote control to start movement of the tool 20 and release the button to stop movement of the tool 20.

D. Force/Torque Sensor

In one version, the manipulator 14 monitors forces and torques placed on the tool 20 in order to position the tool 20. For example, as shown in FIG. 2, the manipulator 14 may comprise a force/torque sensor S. In one implementation, the force/torque sensor S is coupled to the mounting interface 31 of the distal link assembly 29. The mounting interface 31 is configured to receive the end effector 22. The sensed forces and torques may result from various loads. For example, the load may be caused by the tool 20 pressing against tissue or other objects near the surgical site. Alternatively, the medical personnel setting the position and/or orientation of the tool 20 may apply the load. For example, the practitioner may control the manipulator 14 by applying force/torque to the end effector 22 in the manual mode or semi-autonomous mode. The force/torque sensor S may be configured to generate a corresponding input that may be used by the control system 60 (e.g., one or more corresponding input/output signals). In response to the user-applied forces and torques, the manipulator 14 moves the tool 20 in a manner that emulates the movement that would have occurred based on the forces and torques applied by the user. The force/torque sensor S is configured to sense the resulting forces and torques and output signals to the manipulator controller 26, as shown in FIG. 5. The manipulator controller 26 processes the signals to determine control signals for determining a target position for the energy applicator 24 and/or a pose of the manipulator 14. Based on the determination of arm target position, the manipulator controller 26 selectively activates the motors 15 of the manipulator 14 in order to advance the robotic arm R to the target position.

The system, in one implementation, is an admittance-controlled robotic surgical system that utilizes inverse-kinematics to provide a commanded position for the tool 20 and/or end effector 22 based on a solution to a complex system of equations. One variable to the inverse-kinematic solution can be external forces/torques experienced by or applied to the end effector 22, tool 20, or energy applicator 24 by the user or the surgical environment. These external forces/torques can be sensed by the force/torque sensor S. The robotic surgical system accounts for the forces/torques sensed by the force/torque sensor S when determining the commanded position of the tool 20 and/or energy applicator 24. When the force is applied by a user, the robotic surgical system can position the tool 20 and/or energy applicator 24 to emulate the user's intentions. To accurately position the tool 20 and/or energy applicator 24 in these scenarios, it is desirable for the force/torque sensor S to accurately sense such external forces/torques.

Figure 6:
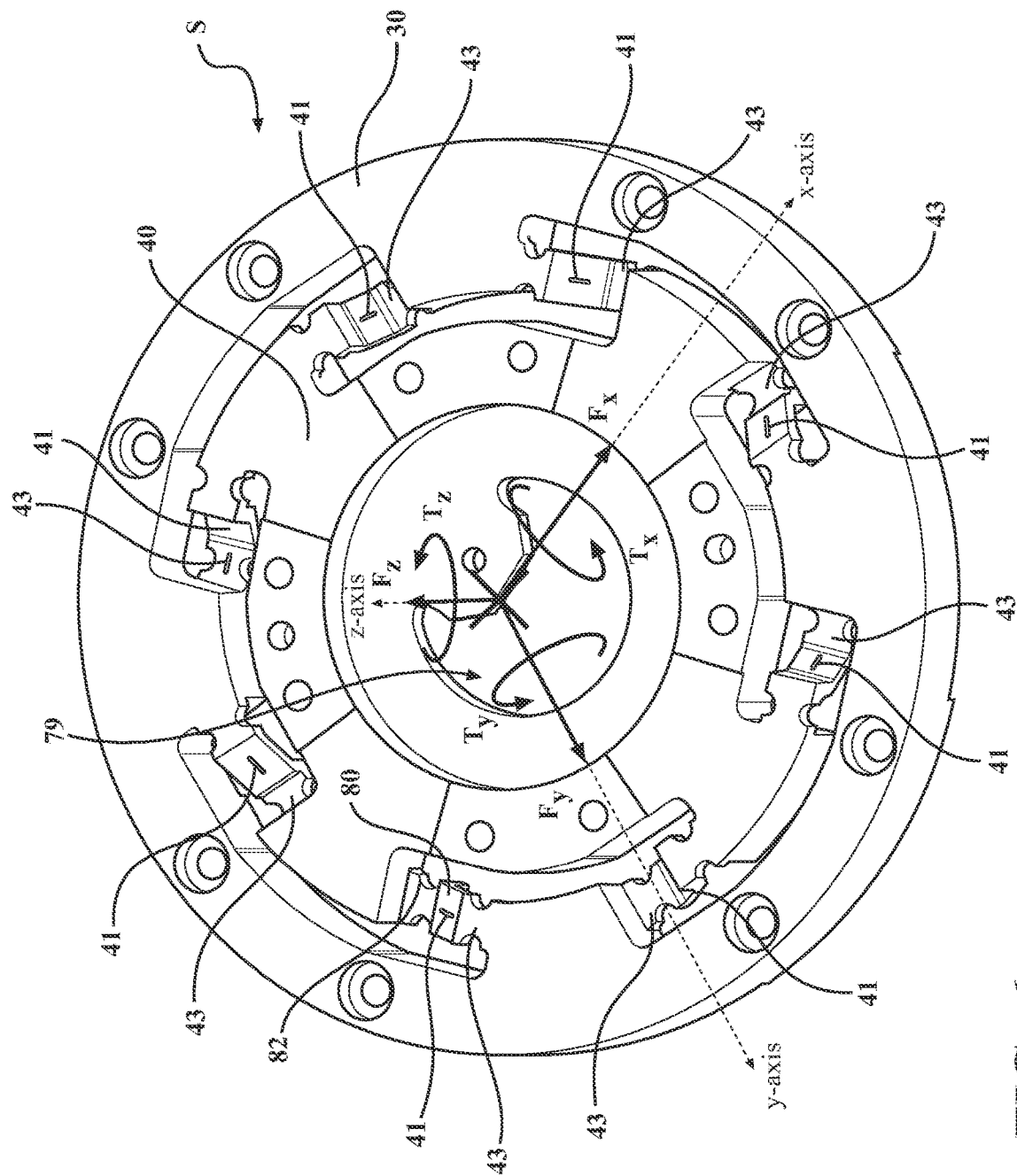
FIG. 6 is a perspective view of an example of a force/torque sensor that can be utilized with the robotic surgical system.

As shown in one implementation of FIG. 6, the force/torque sensor S may include a stationary part 30 and a movable part 40. The movable part 40 is coupled to the stationary part 30 and is configured to be movable relative to the stationary part 30 in response to a load being applied. Additionally, the force/torque sensor S includes sensing elements 41 configured to sense forces ($F_x$, $F_y$, $F_z$) and torques ($T_x$, $T_y$, $T_z$) applied to the movable part 40 as a result of the load. The three components of force ($F_x$, $F_y$, $F_z$) represent axial loads along respective x-, y-, and z-axes. The three components of torque ($T_x$, $T_y$, $T_z$) represent rotational loads about the respective x-, y-, and z-axes. The force/torque sensor S may also include deformable members 43 that connect the stationary part 30 and the movable part 40 and are configured to physically deform from stress resulting upon application of the load to the movable part 40. The sensing elements 41 may be disposed on the deformable members 43 such that the sensing elements 41 sense the sense forces ($F_x$, $F_y$, $F_z$) and torques ($T_x$, $T_y$, $T_z$) applied to the movable part 40 by sensing the deformations of the deformation members 43.

The force/torque sensor S can monitor loads applied to the movable part 40 in many degrees of freedom. In one implementation, the force/torque sensor S monitors loads applied to the movable part 40 in six-degrees of freedom (6DOF). Loads applied to the movable part 40 cause physical strains on the deformable members 43 that are measured and transformed into corresponding forces ($F_x$, $F_y$, $F_z$) and/or torques ($T_x$, $T_y$, $T_z$). Those skilled in the art appreciate that the force/torque sensor S may monitor loads applied to the movable part 40 in any suitable number of DOFs up to 6DOFs.

Figure 7B:
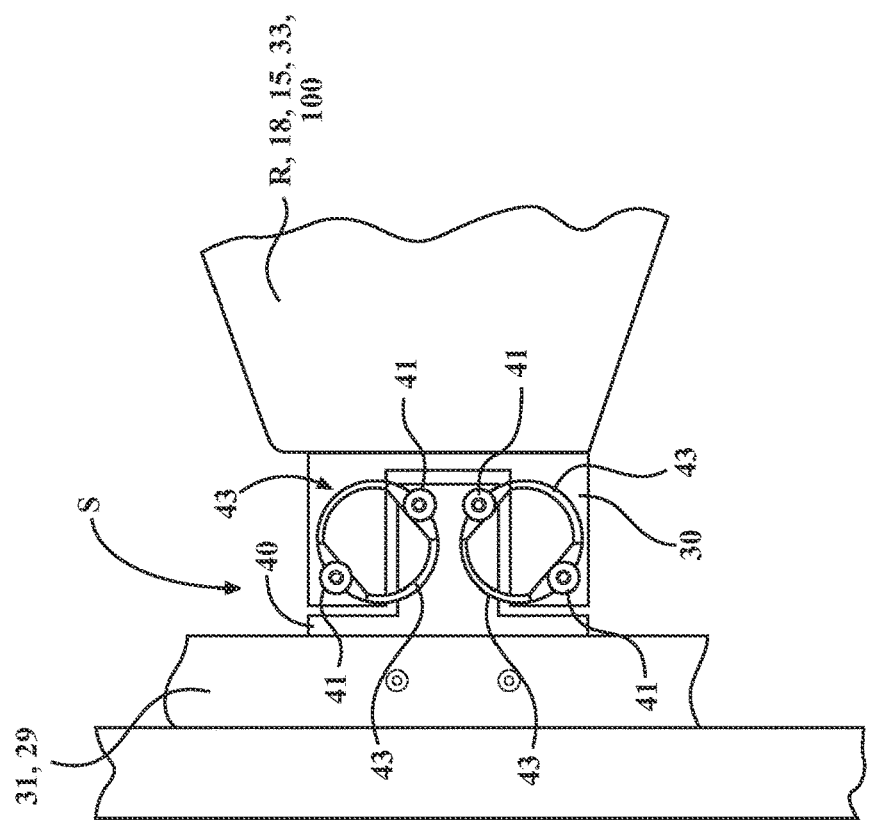
FIG. 7B is an illustration of one example of load cells of a force/torque sensor employed between the end effector and the arm of FIG. 7A.
Figure 7A:
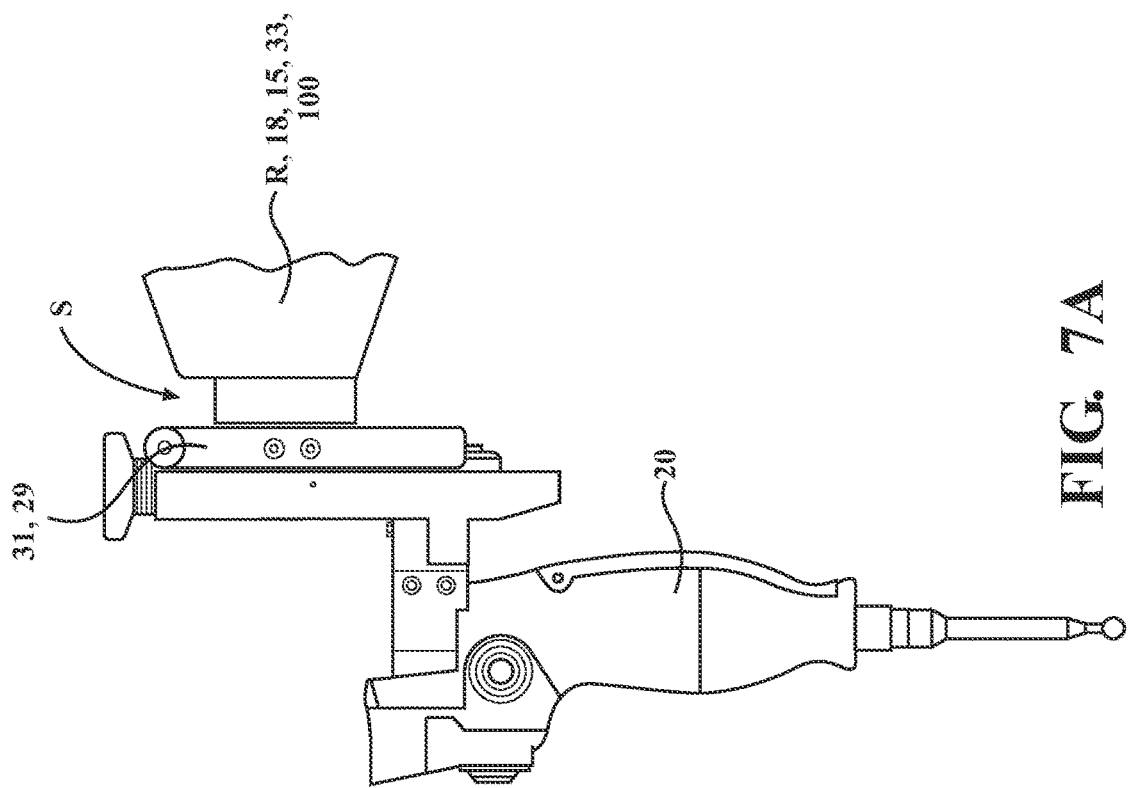
FIG. 7A is a side view of an end effector and an arm of the robotic surgical system, according to one example.

FIGS. 7A and 7B further illustrate one implementation of the force/torque sensors S relative to components of the manipulator 14, including the end effector 22. As generally shown in FIG. 7B, the stationary part 30 of the force/torque sensor S is fixed to the distal link assembly 29 of the robotic arm R, and the movable part 40 of the force/torque sensor S is rigidly attached to the tool 20 or end effector 22. More specifically, the stationary part 30 can be coupled to the isolation mechanism 100 (described in greater detail below), as shown in FIG. 2. The movable part 40 receives the load applied to the tool 20 and moves relative to the stationary part 30 when the load is applied to the tool 20. In response, the deformable members 43 deform, and the sensing elements 41 sense deformation of the deformable members 43 to sense the forces and torques applied to the tool 20.

Referring back to FIG. 6, each deformable member 43 is configured to go into compression or tension upon application of the load to the movable part 40. In some instances, the deformable member 43 may be formed of a more elastic (lower Young's modulus) and/or less dense material than the stationary part 30. In other instances, such as the instance of FIG. 6, the deformable member 43 is formed of the same material as the stationary part 30 but may include a smaller volume or surface area of the material. In other instances, the deformable member 43 may include hollows or perforations such that the deformable member 43 may deform in response to the load. In still other instances, the deformable members 43 may be load cells that are single axis or one degree of freedom (1DOF) load cells and are configured to deform upon application of the load to the movable part 40. The deformation members 43 can take any suitable shape, such as a beam, hoop, pivoting hinge, or the like.

Also shown in FIG. 6, the sensing elements 41 are disposed on the deformable members 43 such that the sensing elements 41 are configured to sense deformation of the deformable members 43. The sensing elements 41 may be any sensor suitable for sensing a force and/or torque of the load applied to the movable part 40. For example, the sensing elements 41 may include a strain gauge for measuring the strain on a deformation member 43. The strain gauge may have wires (not shown) of a resistive element that attach to the surface of the deformation member 43. The strain gauge may be a passive device that changes resistance in response to changes in strain on the surface of the deformation member 43. That is, a length of the wires can change in response to changes in the length of the surface of a deformation member 43. The resistance of the wires changes in response to changes to the length of the electrical wires. Resistance in the strain gauge increases when the surface goes into tension and the resistance in the strain gauge decreases when the surface goes into compression. Strain is proportional to the change in resistance of the strain gauge. The change in resistance is sensed by measuring the voltage across the strain gauge. Any suitable resistance measuring means may measure the change in electrical resistance. Other sensing techniques can be utilized to sense compression/tension of deformation members 43, such as optical or inertial-based force/torque sensors.

The force/torque sensor S in FIG. 6 includes eight sensing elements 41 disposed on eight deformable members 43. In turn, this design provides the possibility for redundant measurements of the load, which can be optimized to improve accuracy or robustness of the force/torque sensor S. In other instances, the force/torque sensor S may include any suitable number of sensing elements 41 and deformable members 43. The force/torque sensor S may include a greater number of sensing elements 41 than deformable members 43, or a greater number of deformable members 43 than sensing elements 41. For example, any suitable number of sensing elements 41 may couple to any one surface, or a number of surfaces, of the deformation members 43. In one such instance, two sensing elements 41 couple to each deformable member 43, wherein one sensing element 41 couples to a first surface 80 of the deformable member 43, and another sensing element 41 couples to a second surface 82 of the deformable member 43. In another instance, four sensing elements 41 may couple to a deformable member 43, wherein two sensing elements 41 may couple to the first surface 80, and two sensing elements 41 couple to the second surface 82. Furthermore, the sensing elements 41 may couple to a deformation member 43 according to any suitable method. For example, the sensing elements 41 may be adhered to a deformation member 43 using an adhesive tape, and the like.

The force/torque sensor S obtains raw gauge values from the sensing elements 41. The manipulator controller 26 may transform the raw gauge values into the resulting forces and torques. For example, the manipulator controller 26 may use a matrix to convert gauge measurements into force and torque measurements, such as the matrix M described in U.S. Pat. No. 9,993,309, filed on Feb. 3, 2016, entitled "Force/Torque Transducer and Method of Operating the Same," the disclosure of which is hereby incorporated by reference.

The force/torque sensor S may include any suitable structure. For example, the force/torque sensor S in FIG. 6 includes a planar cylindrical configuration. The force/torque sensor S also includes an opening 79 formed within an axial center (illustrated using an "X"), the opening 79 being cylindrically-shaped. In other instances, the force/torque sensor S may include a cuboidal or prismatic configuration and the force/torque sensor S may optionally omit the opening 79. Additionally, the force/torque sensor S may also be any force/torque sensor described in U.S. Pat. No. 9,993,309, the disclosure of which is hereby incorporated by reference.

In some versions, measurements taken by the force/torque sensor S are transformed from a force/torque coordinate system FT of the force/torque sensor S to another coordinate system, such as a virtual mass coordinate system in which a virtual simulation is carried out on the virtual rigid body model of the tool 20 so that the forces and torques can be virtually applied to the virtual rigid body in the virtual simulation to ultimately determine how those forces and torques (among other inputs) would affect movement of the virtual rigid body.

The force/torque sensor S is not intended to be limited specifically to the examples shown and described. Those skilled in the art can implement the force/torque sensor S in a variety of different ways, with or without the features described above.

II. Isolation Mechanism and Techniques

The manipulator 14 may also include an isolation mechanism 100. As shown, for example, in FIG. 2, the isolation mechanism 100 is coupled to the force/torque sensor S and to the transmission 33, represented as a strain wave gear transmission 33' of FIG. 2. As described above, the techniques described herein may be utilized with transmissions other than strain wave gear transmissions.

Figure 8B:
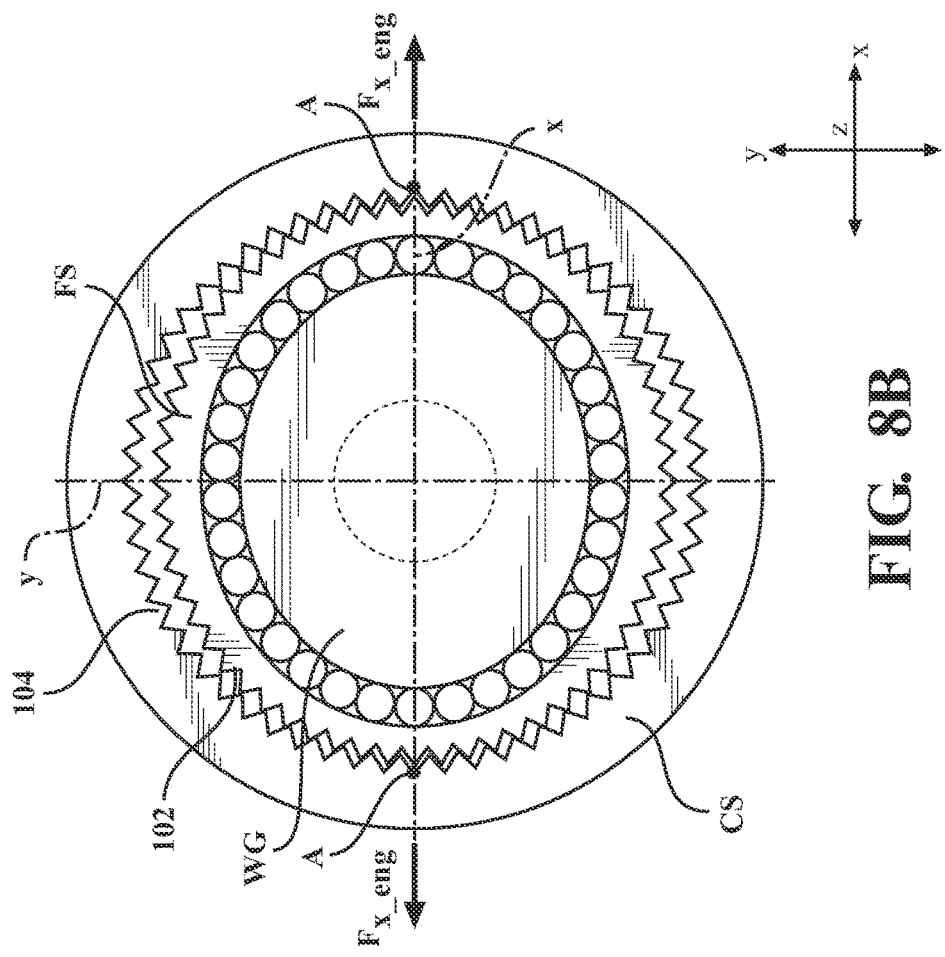
FIGS. 8A and 8B are diagrammatic views of one example of a wave generator of the strain wave generator rotating within a circular spline of the strain wave gear transmission of FIG. 3A.
Figure 8A:
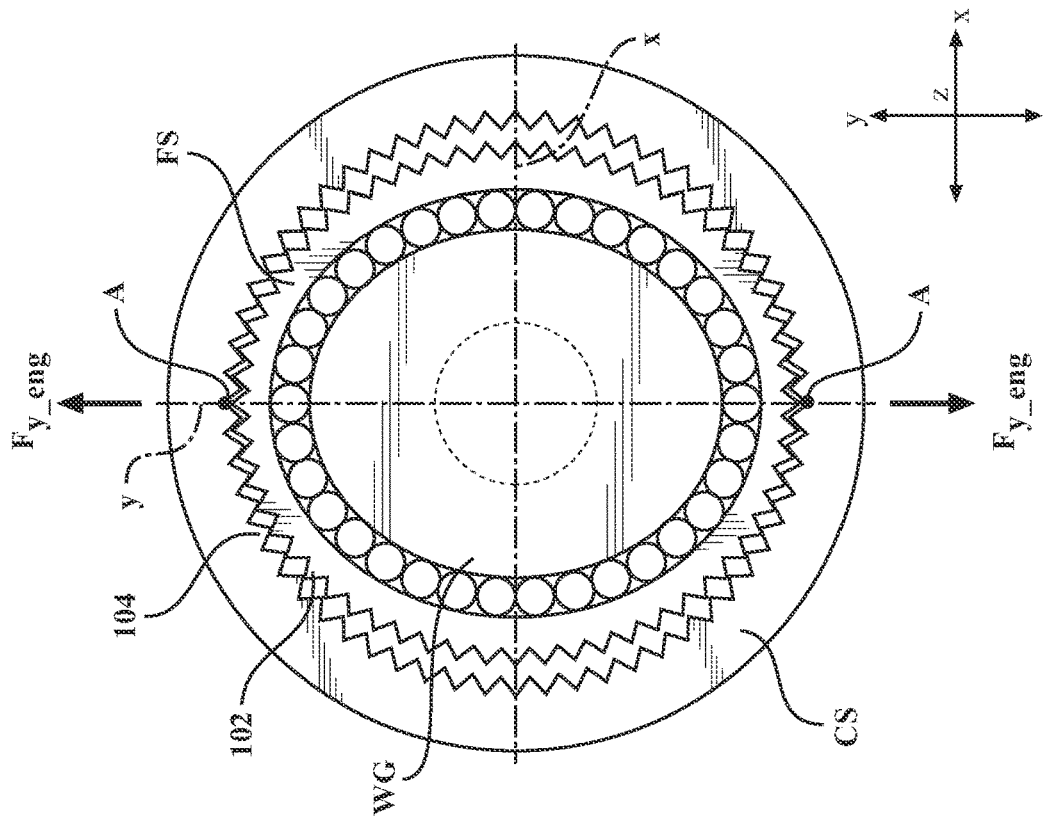

The isolation mechanism 100 is configured to deform in response to forces induced by the transmission 33. FIGS. 8A and 8B illustrate one example of forces induced by a strain wave gear transmission 33'. As the wave generator WG rotates, the flex spline FS rotates, causing the teeth 102 of the flex spline FS to engage the teeth 104 of the circular spline CS. The engagement of the teeth 102 of the flex spline FS and the teeth 104 of the circular spline CS, illustrated as engagement A in FIGS. 8A and 8B, induces forces that are applied to the circular spline CS. As shown, the engagement may induce the forces $F_{y\_eng}$ and $F_{x\_eng}$, which are applied to the circular spline CS, causing potential deformation of the circular spline CS. As a result, in instances where the strain wave gear transmission 33' is directly coupled to the force/torque sensor S, the induced forces causes the circular spline CS to exert corresponding forces on the force/torque sensor S.

In FIGS. 8A, and 8B, the engagement A of the teeth 102 of the flex spline FS and the teeth 104 of the circular spline CS induces the forces $F_{y\_eng}$ and $F_{x\_eng}$, which are coplanar to a surface of the strain wave gear transmission 33'. Force $F_{y\_eng}$ is generated when the engagement A occurs along the y-axis, as labeled in FIGS. 8A and 8B. Force $F_{x\_eng}$ is generated when the engagement A occurs along the x-axis, as labeled in FIGS. 8A and 8B. The engagement A may also induce forces or torques that are not shown in FIGS. 8A and 8B. For example, the engagement A may induce a force along a z-axis (not shown), which is perpendicular to the x-axis and y-axis. Additionally, the engagement A may induce a force that is a combination of forces $F_{y\_eng}$, $F_{x\_eng}$, and forces along the z-axis. The transmission 33' can also induce torque about the z-axis.

The isolation mechanism 100 is configured to deform in response to forces induced by the transmission 33 in order to mechanically isolate the force/torque sensor S from forces induced by the transmission 33. As previously stated, in response to external or user-applied forces and torques, the force/torque sensor S provides signals which can provide input to control of the manipulator 14. In instances where the transmission 33 is coupled to the force/torque sensor S, without presence of the isolation mechanism 100 therebetween, the forces exerted by the transmission 33 have the potential to cause an error condition wherein such exerted forces may physically influence movement of components of the force/torque sensor S. In turn, such error can affect the force/torque readings of the force/torque sensor S, and consequently, control of the manipulator 14.

To mitigate this error, the isolation mechanism 100 is provided to isolate the force/torque sensor S from such influences. As a result, the force/torque sensor S is able to accurately sense applied forces and/or torques substantially free from interference from forces induced by the transmission 33. Ideally, the isolation mechanism 100 completely isolates the force/torque sensor S such that no forces are induced to the force/torque sensor S by the transmission 33. However, complete isolation may be impractical due to restrictions involved with sizing or rigidity of the isolation mechanism 100 due to the robotic design requirements. Hence, substantially free from interference can mean that the forces induced by the transmission 33 are substantially isolated from the force/torque sensor S so that such forces have a zero or negligible adverse effect on robotic control.

Figure 9A:
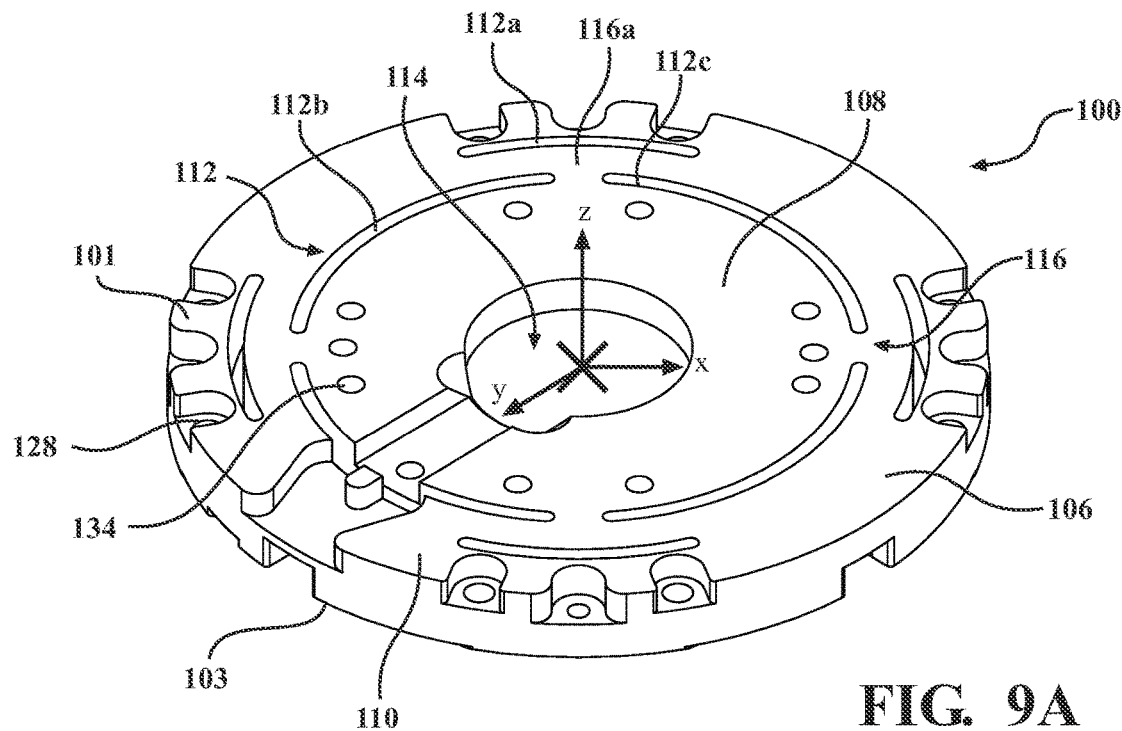
FIG. 9A is a perspective view of one example of an isolation mechanism that can be utilized with the robotic surgical system.
Figure 9B:
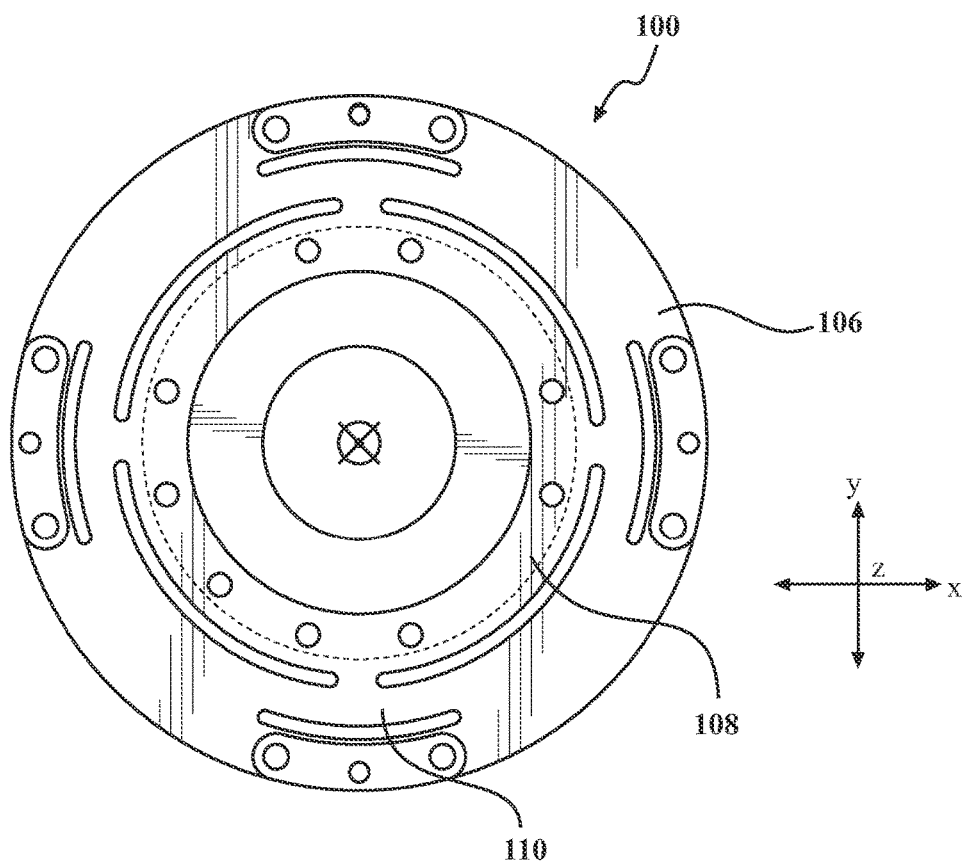
FIG. 9B is a top view of the isolation mechanism of FIG. 9A with an elastic part and a rigid part of the isolation mechanism delineated using dotted lines according to one implementation.

As shown in one implementation of FIGS. 9A and 9B, the isolation mechanism 100 may include a body 106, which includes at least one rigid part 108 and at least one elastic part 110. Referring to FIG. 9B, in this example, the isolation mechanism 100 includes a rigid part 108 and an elastic part 110, the regions of which are delineated using dotted lines, according to one implementation. Depending on the configuration of the isolation mechanism 100, delineation between the rigid and elastic parts 108, 110 may be defined according to geometry more complex than the example shown in FIG. 9B. For example, rigid and elastic parts 108, 110 may be delineated by regions that are completely isolated from one other, partially isolated from one another, or overlapping one another. Furthermore, delineation of the rigid and elastic parts 108, 110 may vary (increase or decrease in size) for the same isolation mechanism 100 depending on how the isolation mechanism is coupled to the transmission 33 and the force/torque sensor S, the nature or type of deformation exhibited by the output of the transmission 33, and the geometry and/or configuration of the isolation mechanism 100. While FIG. 9B shows one implementation of how the rigid and elastic parts 108, 110 may be delineated, it is contemplated that the position of the rigid and elastic parts 108, 110 can be swapped as compared to the configuration shown in FIG. 9B. The rigid and elastic parts 108, 110 may also include any suitable shape.

Additionally, the term "part" with reference to elastic and rigid part is intended to define structural functions of certain regions of the body 106 of the isolation mechanism 100. The term "part" does not necessarily require that these be separate or separable parts. The rigid and elastic parts 108, 110 may be separate components that are attached to one another or may be formed of a common structure or material having rigid and elastic regions or portions.

The isolation mechanism 100 may include any suitable number of elastic parts 110 and rigid parts 108. For example, in FIGS. 9A and 9B, the isolation mechanism 100 includes one rigid part 108 and one elastic part 110. In other instances, the isolation mechanism 100 can comprise: two rigid parts 108 and one elastic part 110; one rigid par 108 and two elastic parts 110; two rigid parts 108 and two elastic parts 110; or "N" rigid parts 108 and "M" elastic parts 110, where N and M are greater than or equal to one.

Figure 10:
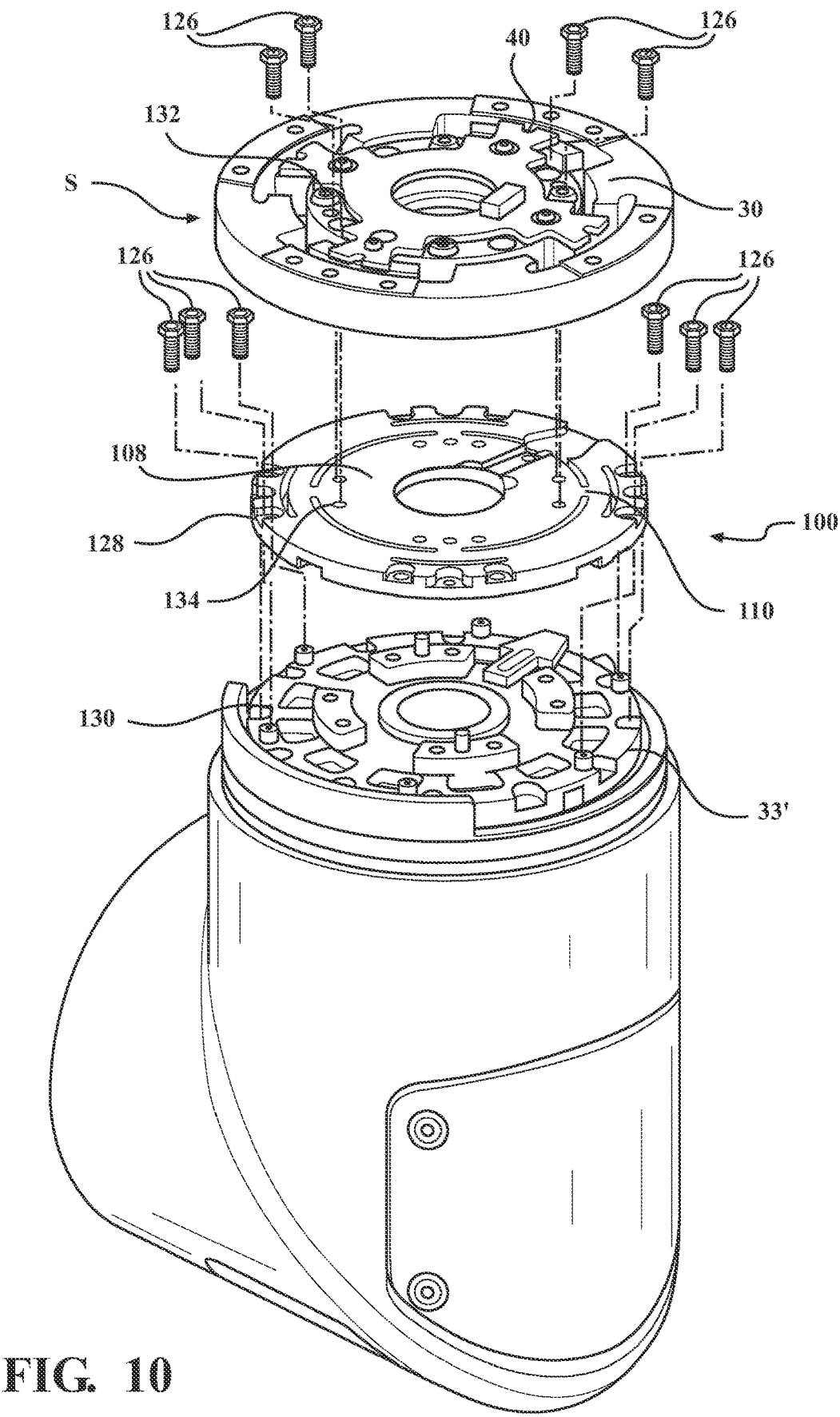
FIG. 10 is an exploded view illustrating one instance of coupling of the isolation mechanism of FIG. 9A to the force/torque sensor of FIG. 6 and the strain wave gear transmission of FIG. 3A.

As shown in FIGS. 2 and 10, the isolation mechanism 100 may be coupled to the output of the transmission 33, and to the force/torque sensor S. The elastic part 110 or the rigid part 108 of the isolation mechanism 100 can be coupled to the output of the transmission 33, e.g., the strain wave gear transmission 33'. In other words, either the rigid part 108 or the elastic part 110 can be coupled to the output of the strain wave gear transmission 33'. Where the isolation mechanism 100 comprises more than one rigid part 108 or more than one elastic part 110, either one of the rigid parts 108 or either one of the elastic parts 110 is coupled to the output of the strain wave gear transmission 33'. For example, referring to FIG. 10, the elastic part 110 is coupled to the output of the strain wave gear transmission 33'.

The elastic part 110 or the rigid part 108 of the isolation mechanism 100 can be coupled to the force/torque sensor S. In other words, either the rigid part 108 or the elastic part 110 can be coupled to the force/torque sensor S. Where the isolation mechanism 100 comprises more than one rigid part 108 or more than one elastic part 110, either one of the rigid parts 108 or either one of the elastic parts 110 is coupled to the force/torque sensor S. For example, referring to FIG. 10, the rigid part 108 is coupled to the force/torque sensor S.

The isolation mechanism 100 is further coupled to one of the stationary part 30 and the movable part 40 of the force/torque sensor S. In other words, either the rigid part 108 or the elastic part 110 can be coupled to the stationary part 30, or either the rigid part 108 or the elastic part 110 can be coupled to the movable part 40, of the force/torque sensor S. Where the isolation mechanism 100 comprises more than one rigid part 108 or more than one elastic part 110, either one of the rigid parts 108 or either one of the elastic parts 110 can be coupled to one of the stationary part 30 and the movable part 40 of the force/torque sensor S. For example, referring to FIG. 10, the rigid part 108 is coupled to the movable part 40 of the force/torque sensor S. In some instances, the isolation mechanism 100 may include an opening 114 such that, when the isolation mechanism 100 is coupled to the force/torque sensor S, the opening 79 of the force/torque sensor S (shown in FIG. 6) is aligned with an opening 114 of the isolation mechanism 100 (shown in FIG. 9A).

The elastic part 110 and the rigid part 108 may be coupled to the transmission 33 and the force/torque sensor S using any suitable method. For example, referring to FIG. 10, the elastic part 110 is coupled to the strain wave gear transmission 33' using bolts 126 that are inserted into holes 128 of the elastic part 110 and holes 130 of the strain wave gear transmission 33'. Similarly, the rigid part 108 is coupled to the movable part 40 of the force/torque sensor S using bolts 126 that are inserted into holes 132 of the force/torque sensor S and holes 134 of the rigid part 108. The isolation mechanism 100 may also include any suitable number of holes for coupling to the strain wave gear transmission 33' and the force/torque sensor S. For example, in the various instances of FIGS. 9A-15A, the elastic parts 110 are shown as including three to twelve holes 128 and the rigid parts 108 are shown as including three to twelve holes 134. In other instances, the rigid part 108 may include any other suitable number and arrangement of holes for coupling. For example, in instances where the rigid part 108 is coupled to the strain wave gear transmission 33' and/or the force/torque sensor S, the rigid part 108 may include any suitable number and arrangement of holes for coupling. The isolation mechanism 100 may be coupled to the transmission 33 and the force/torque sensor S using other fasteners, such as screws, pegs, pins, rivets, etc. The isolation mechanism 100 may also be coupled to the transmission 33 and the force/torque sensor S using adhesives, such as epoxies, cyanoacrylates, urethanes, or acrylic adhesives. The isolation mechanism 100 may also be coupled to the transmission 33 and the force/torque sensor S using a fabrication process, such as welding, brazing, or soldering.

Figure 11B:
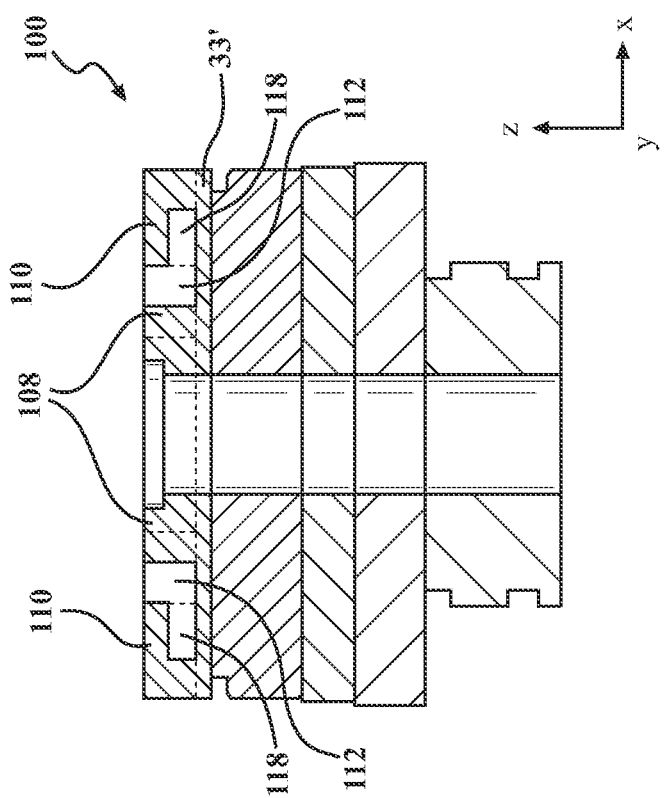
FIGS. 11A and 11B are an exploded view and a side view, respectively, of an example of the isolation mechanism being monolithically formed with an output of the strain wave gear transmission.
Figure 11A:
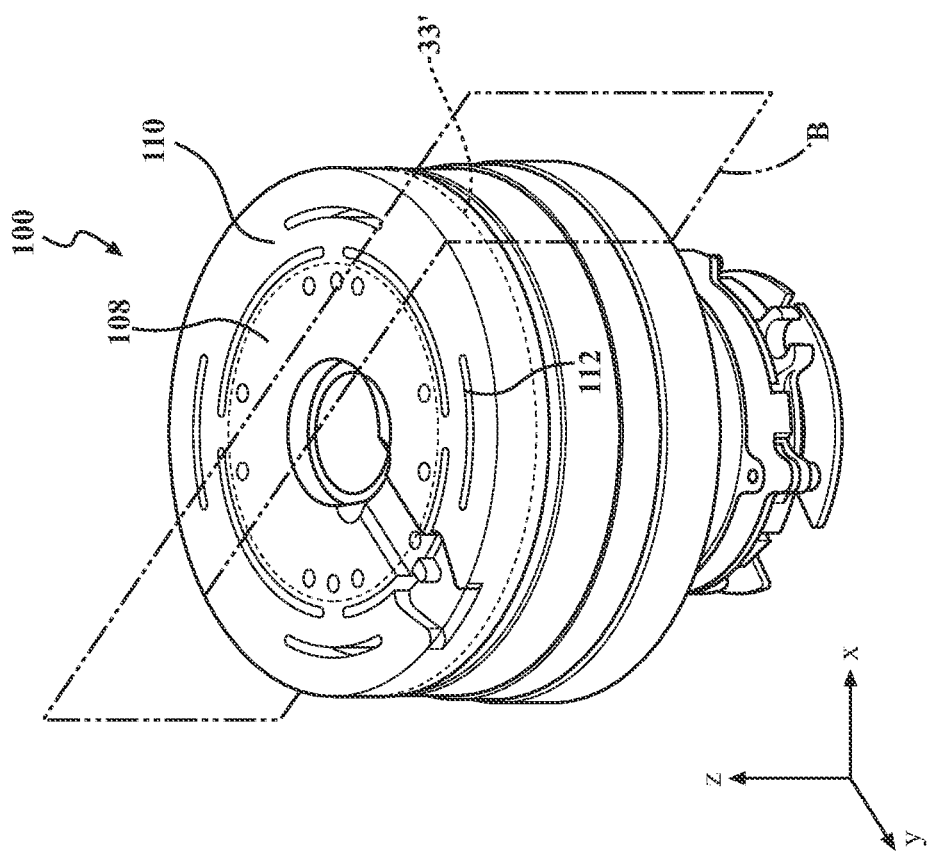

The isolation mechanism 100 may be monolithically formed with the output of the transmission 33. Specifically, the rigid part 108 and/or the elastic part 110 may be monolithically formed with the output of the transmission 33. In the example of FIGS. 11A and 11B, the rigid part 108 and the elastic part 110, delineated using dotted lines, are both monolithically formed with the output of the strain wave gear transmission 33'. In FIGS. 11A and 11B, the rigid part 108 and the elastic part 110 are monolithically formed with the strain wave gear transmission 33' by being formed with, or of the same material as, the strain wave gear transmission 33'. In another instance, one of the rigid part 108 and the elastic part 110 may be monolithically formed with the strain wave gear transmission 33'. In such an instance, the one of the rigid part 108 and the elastic part 110 that is monolithically formed with the strain wave gear transmission may be formed of the same material as the strain wave gear transmission 33'.

A portion of the elastic part 110 may be separated from the transmission 33 in instances where the elastic part 110 is monolithically formed with the output of the transmission 33. For example, referring to FIG. 11B, a cross-sectional view of the isolation part 100 and the transmission 33' is shown, where the cross-sectional view is along the plane B, shown in FIG. 11A. In FIG. 11B, the elastic part 110 includes an opening 118 between a portion of the elastic part 110 and the strain wave gear transmission 33' such that the portion of the elastic part 110 is separated from the strain wave gear transmission 33'. In the instance of FIG. 11B, the opening 118 is integral to a hollow 112 of the elastic part 110. In other instances, the opening 118 may be separated from the hollow 112. In still other instances, the elastic part 110 may optionally omit the opening 118.

The elastic part 110 and the rigid part 108 of the isolation mechanism 100 may be arranged in any suitable fashion relative to one another. For example, in FIGS. 9A and 9B, the elastic part 110 and the rigid part 108 are arranged such that the elastic part 110 is disposed concentrically about the rigid part 108. In other instances, such as where the isolation mechanism 100 includes two elastic parts 110 and one rigid part 108, a rigid part 108 may be disposed between the two elastic parts such that a first elastic part 110 is disposed concentrically about the rigid part 108, and the rigid part 108 is disposed concentrically about the second elastic part 110.

In some instances, the elastic part 110 and the rigid part 108 may be arranged on separate planes that are perpendicular to a central axis defined through a center of the body 106, as illustrated in FIGS. 12-15. The central axis defined through the center of the body 106 can be the z-axis, with the center of the body 106 illustrated using an "X". Referring to FIGS. 12A-15F, planes 120 and 122 perpendicular to the z-axis extend through a center of the elastic part 110 and a center of the rigid part 108, respectively. As shown, the planes 120, 122 are arranged at different locations along the z-axis.

The at least one elastic part 110 of the isolation mechanism 100 is configured to deform in response to the forces induced by the transmission 33 in order to mechanically isolate the force/torque sensor S from forces induced by the transmission 33.

The elastic part 110 is defined as being more elastic (or less rigid) than the rigid part 108. Said differently, the rigid part 108 is defined as being more rigid (or less elastic) than the elastic part 110. Due to the reality that no component is infinitely rigid, it is contemplated that the rigid part 108 may also be configured to deform in response to the forces induced by the transmission 33.

In one implementation, greater elasticity of the elastic part 110 can be accomplished by changing material properties or characteristics of the body 106. For example, the elastic part 110 may have a lower Young's modulus, the modulus of elasticity in tension, than the rigid part 108. As an example, the elastic part 110 may have a Young's modulus within a range of 115-130 GPa and the rigid part 108 may have a Young's modulus within a range of 145-180 GPa. Additionally, or alternatively, the elastic part 110 may be formed of a less dense material than the rigid part 108. In other instances, the elastic part 110 and the rigid part 108 may be formed of the same material; however, the elastic part 110 may be more elastic because the elastic part 110 may have a smaller volume, surface area, or thickness of the material as compared with the rigid part 108. In another instance, the elastic part 110 may be more elastic than the rigid part 108 because the rigid part 108 is connected and fixed to a component of the manipulator 14 (e.g., the force/torque sensor S or the transmission 33), whereas as the elastic part 110 is not connected to a component of the manipulator 14. In other examples, elasticity may be accomplished by springs and/or dampers disposed between rigid parts 108. Here, the springs and/or dampers can be considered the elastic parts 110. If utilized, the springs/dampers comprise sufficient rigidity to support the weight of the distal link assembly 29 and downstream components, such as the force/torque sensor S, the end effector and the surgical tool. Any of these techniques can be utilized individually or in combination.

Additionally, or alternatively, removed material, or absence of material, of the body 106, may enable the elastic part 110 to exhibit greater elasticity than the rigid part 108. Specifically, the isolation mechanism 100 may include hollows 112, such as bores, holes, slots, apertures, openings or perforations defined between a first surface 101 and a second surface 103, such as shown in FIG. 9A, for example. Where present, these hollows 112 can define the region of the elastic part 110 of the body 106.

Even though the elastic part 110 is deformable, the elastic part 110 is designed to be rigid enough to physically support the weight of downstream components of a robotic arm R, such as the joint J6, force torque sensor S, end effector 22 and the tool 20, as well as any other components of the manipulator 14. Hence, the elastic part 110 is defined to be rigid enough such that the manipulator 14, when commanded, can rigidly and accurately control a state (position and/or orientation) of the tool 20 (e.g., the TCP). If the elasticity or deformability of the isolation mechanism 100 were designed to be greater than a certain threshold, the rigidity and accuracy of the manipulator 14 may potentially be compromised. If the elasticity or deformability of the isolation mechanism 100 were designed to be below a certain threshold, the isolation mechanism 100 potentially may not be able to isolate the force/torque sensor S from forces induced by the transmission. In one instance, the elasticity of the elastic part 110 may allow for greater than 80% isolation from forces induced by the transmission, while causing less than 5% stiffness loss in the manipulator 14. In other instances, the elasticity of the elastic part 110 may allow for greater than 70% isolation from forces induced by the transmission, while causing less than 10% stiffness loss in the manipulator 14.

Figure 15A:
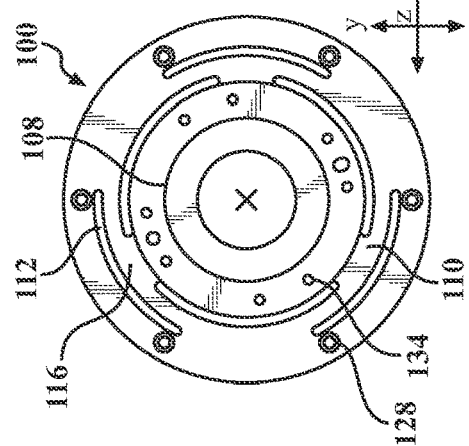
FIGS. 15A-15G are top views of various implementations of the isolation mechanism including a variety of notches and elastic segments.
Figure 15B:
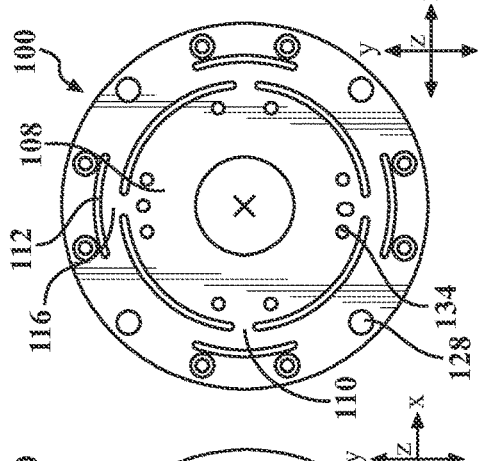
Figure 15C:
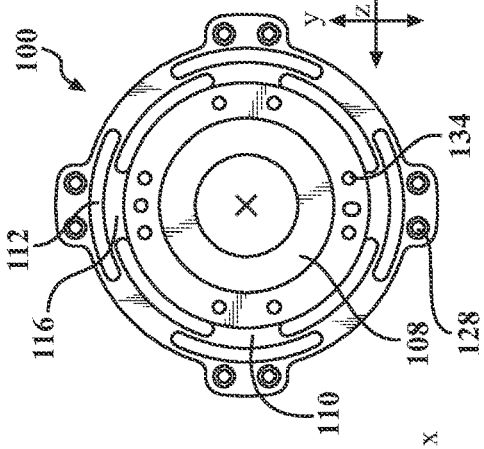
Figure 15D:
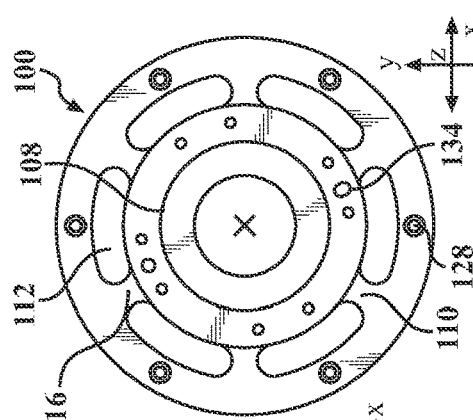
Figure 15E:
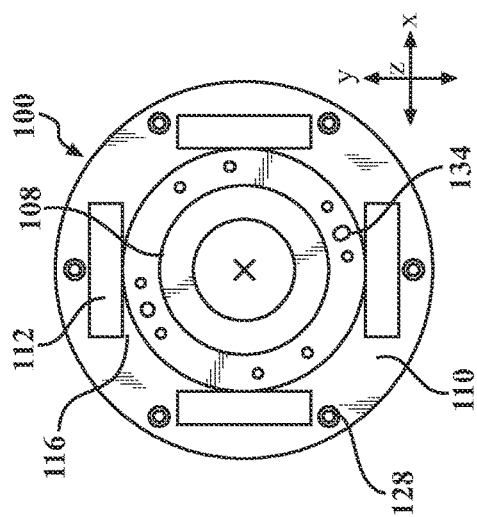
Figure 15F:
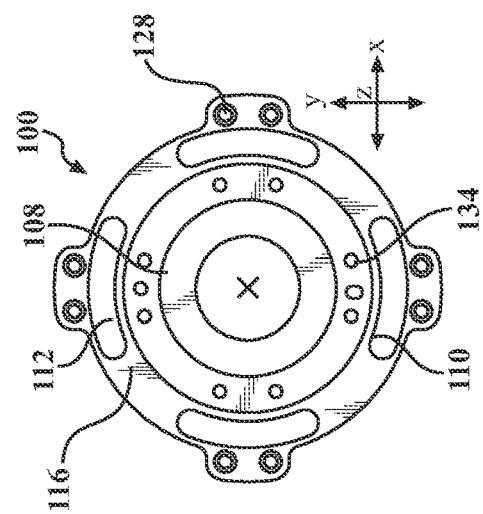
Figure 15G:
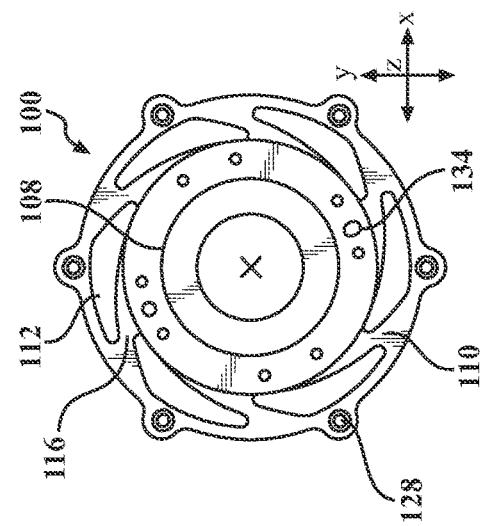

FIGS. 15A-15G illustrate various implementations of the isolation mechanism 100. Here, different configurations of the hollows 112 are illustrated. As shown, the elastic parts 110 may be defined by any suitable number of hollows 112. For example, the elastic part 110 may be defined by four hollows 112 (as shown in FIGS. 15F and 15G), six hollows 112 (as shown in FIGS. 15A and 15D-15E), eight hollows 112 (as shown in FIGS. 15B-15C), or any other suitable number of hollows 112. The hollows 112 may also include any suitable shape, which can be utilized as one type or a combination of different types. For example, the hollows 112 may include a curved or radial shape (as shown in FIGS. 15A-15C), a round or oval shape (as shown in FIGS. 15D and 15F), a spiral shape (as shown in 15E), a polygonal shape (as shown in FIG. 15G), or the like. The hollows 112 may also include any suitable size, and different-sized hollows 112 can be utilized. For example, a size of the hollows 112 at either the first surface 101 or the second surface 103 may vary. The dimensions of the hollows 112 can also vary between the first and second surfaces 101, 103. The hollows 112 may also be arranged in any suitable fashion. For example, the hollows 112 may be arranged about an axial center of the body 106, illustrated using an "X", in a single concentric grouping (as shown in FIGS. 15D, 15E, and 15F) or a plurality of concentric groupings (as shown in FIGS. 15A, 15B, 15C). The hollows 112 may also be radial to the axial center (as shown in FIGS. 15A-15F) or transverse to the axial center (as shown in FIG. 15G).

In some instances, the hollows 112 cause the elastic part 110 to be more elastic than the rigid part 108 by defining a plurality of elastic segments 116 adjacent to the hollows 112. For example, in FIG. 9A, the elastic segments 116 of the elastic part 110 are connected to the rigid part 108. The elastic segments 116 are configured to deform in any suitable direction to enable the elastic part 110 of the isolation mechanism 100 to deform.

FIGS. 9A and 15A-15G illustrate various instances of the elastic segments 116. As shown, the elastic segments 116 include a variety of shapes. The geometrical configuration of each elastic segment 116 may be defined in part by hollows 112 formed adjacent to each elastic segment 116. The geometrical configuration of each elastic segment 116 may be defined by the number of hollows 112 adjacent to each elastic segment 116. For example, the geometrical configuration of an elastic segment 116a in FIG. 9A is defined by three hollows 112—an upper hollow 112a and two lateral hollows 112b, 112c. Similarly, in FIGS. 15A-15C, the geometrical configuration of each elastic segment 116 is defined by three hollows 112. In contrast, the geometrical configuration of each elastic segment 116 in FIGS. 15D-15F is defined by two hollows 112. The geometrical configuration of each elastic segment 116 may also be defined by the shape of the hollows 112 adjacent to each elastic segment 116. For example, in FIG. 9A, the geometrical configuration of the elastic segment 116a is defined by the rounded shape of the adjacent hollows 112a, 112b, 112c.

Figure 13B:
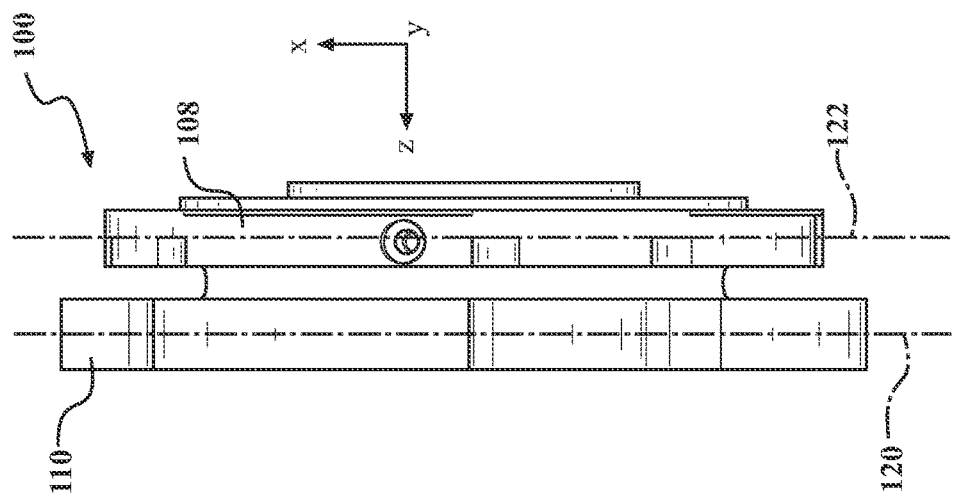
FIGS. 13A and 13B are a perspective view and a side view, respectively, of an example of the isolation mechanism where an elastic part and a rigid part of the isolation mechanism are arranged on separate planes along a z-axis.
Figure 13A:
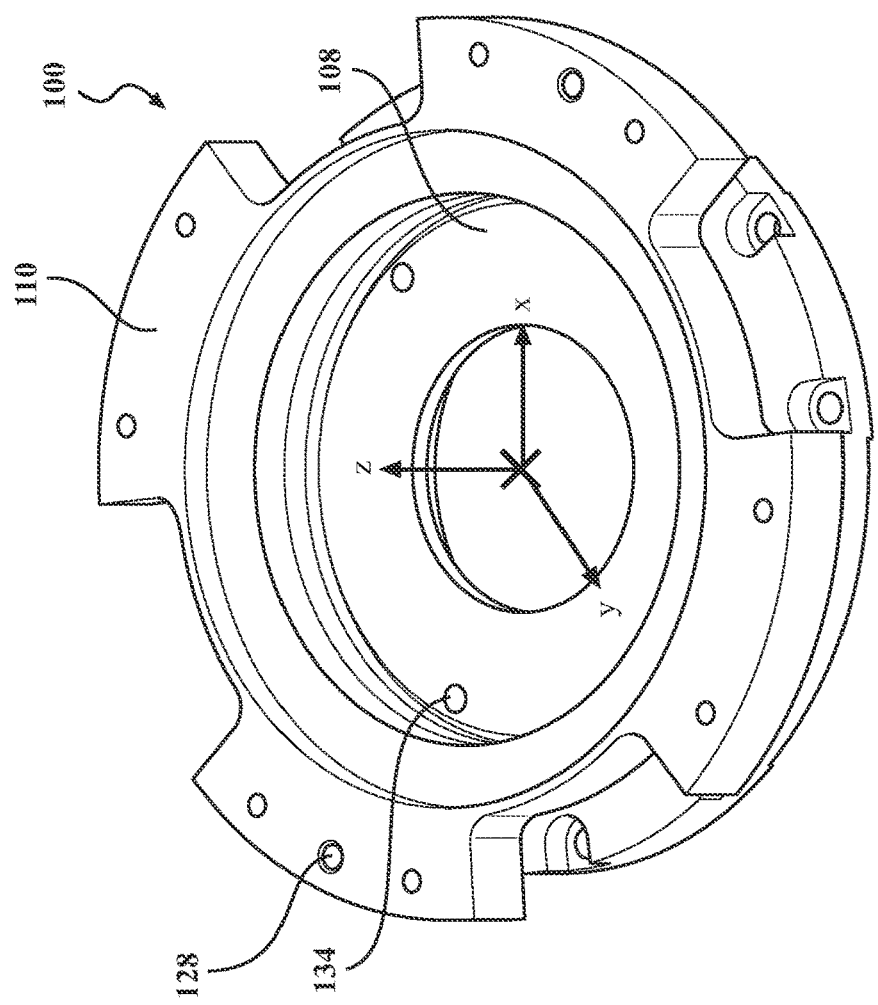

The elastic part 110 can comprise any number of hollows 112 and elastic segments 116. For example, the elastic part 110 can comprise: eight hollows 112 and four elastic segments 116 (as shown in FIG. 9A); six hollows 112 and six elastic segments 116; or "M" hollows 112 and "M" elastic segments 116, where M is greater than or equal to one. Additionally, the elastic part 110 may optionally be without hollows 112 or elastic segments 116, as shown in the example of FIG. 13A.

Figure 12B:
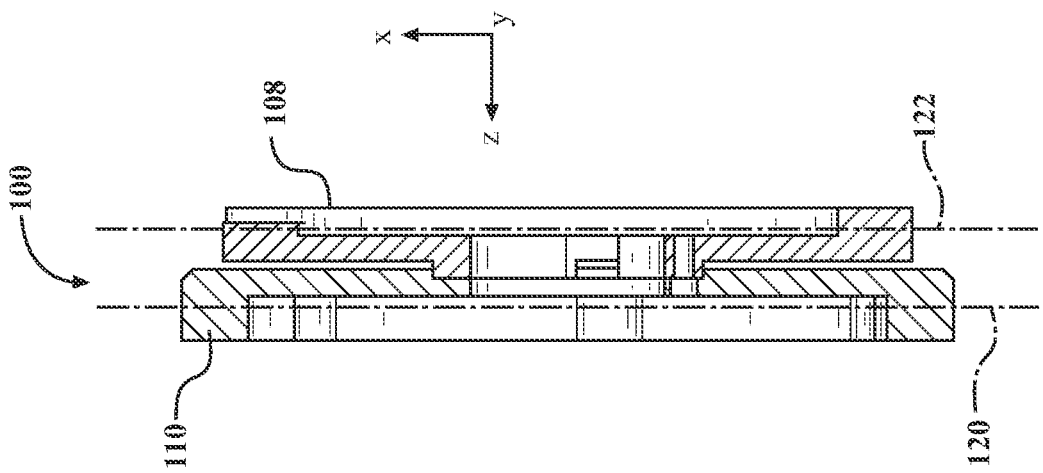
FIGS. 12A and 12B are a perspective view and a side view, respectively, of an example of the isolation mechanism where an elastic part and a rigid part of the isolation mechanism are arranged on separate planes along a z-axis.
Figure 12A:
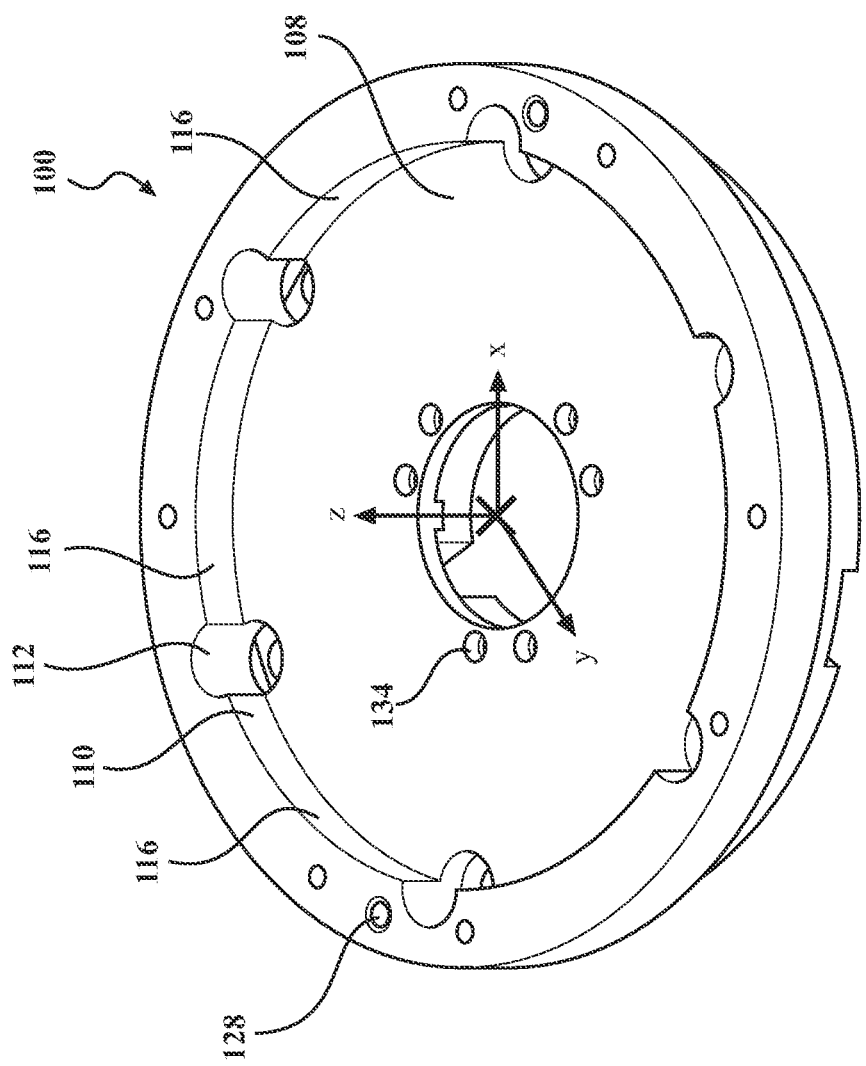

The body 106 may include any suitable planar or non-planar configuration. For example, the body 106 in FIG. 9A includes a planar configuration, wherein the rigid part 108 and the elastic part 110 are substantially coplanar. FIGS. 12-14 illustrate instances where the body 106 has a multi-planar configuration. As shown, the rigid part 108 and the elastic part 110 are arranged on separate planes 120, 122, 124, respectively, that are perpendicular to the z-axis. In other instances, the body 106 may include any other suitable configuration, such as a cuboidal configuration, a prismatic configuration, or a spherical configuration.

Figure 16B:
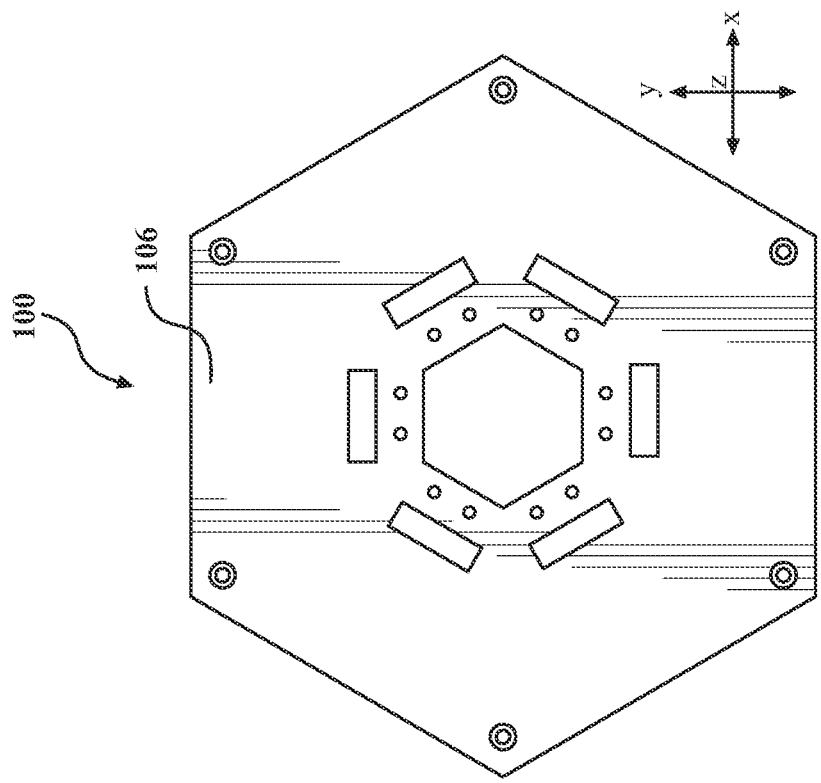
FIGS. 16A-16B are top views of additional implementations of the isolation mechanism.
Figure 16A:
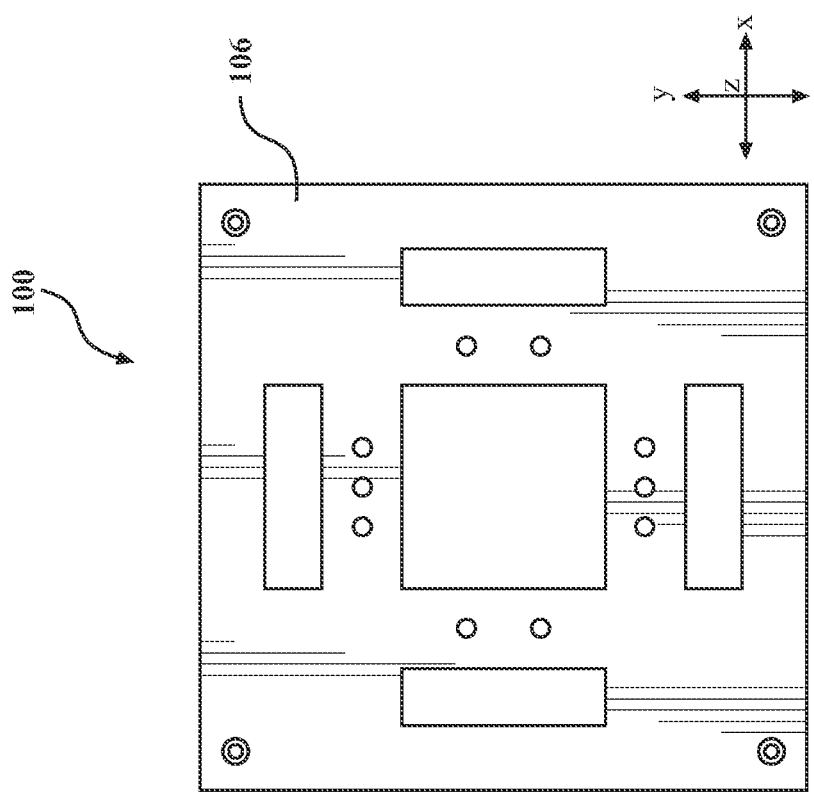

The body 106 of the isolation mechanism 100 may include any suitable shape or any cross-sectional configuration. In some instances, the body 106 may include a cross-sectional configuration to similar to, or to accommodate, a shape of a cross-section of the force/torque sensor S or the output of the transmission 33. For example, the isolation mechanism 100 in FIG. 9A includes a circular cross-sectional configuration. FIGS. 16A and 16B illustrate other example cross-sectional configurations of the body 106. For example, the body 106 in FIG. 16A includes a quadrilateral cross-sectional configuration and the body 106 in FIG. 16B includes a hexagonal cross-sectional configuration. In other instances, the body 106 may include an elliptical, oval, triangular, trapezoidal, rhomboidal, octagonal, polygonal, concave, convex, or any irregular shaped cross-sectional configuration, or the like.

Figure 14B:
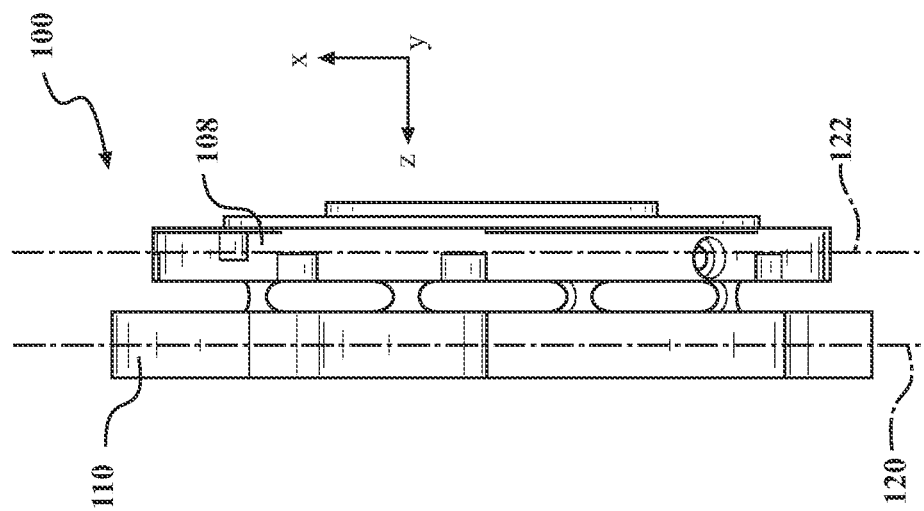
FIGS. 14A and 14B are a perspective view and a side view, respectively, of an example of the isolation mechanism where an elastic part and a rigid part of the isolation mechanism are arranged on separate planes along a z-axis.
Figure 14A:
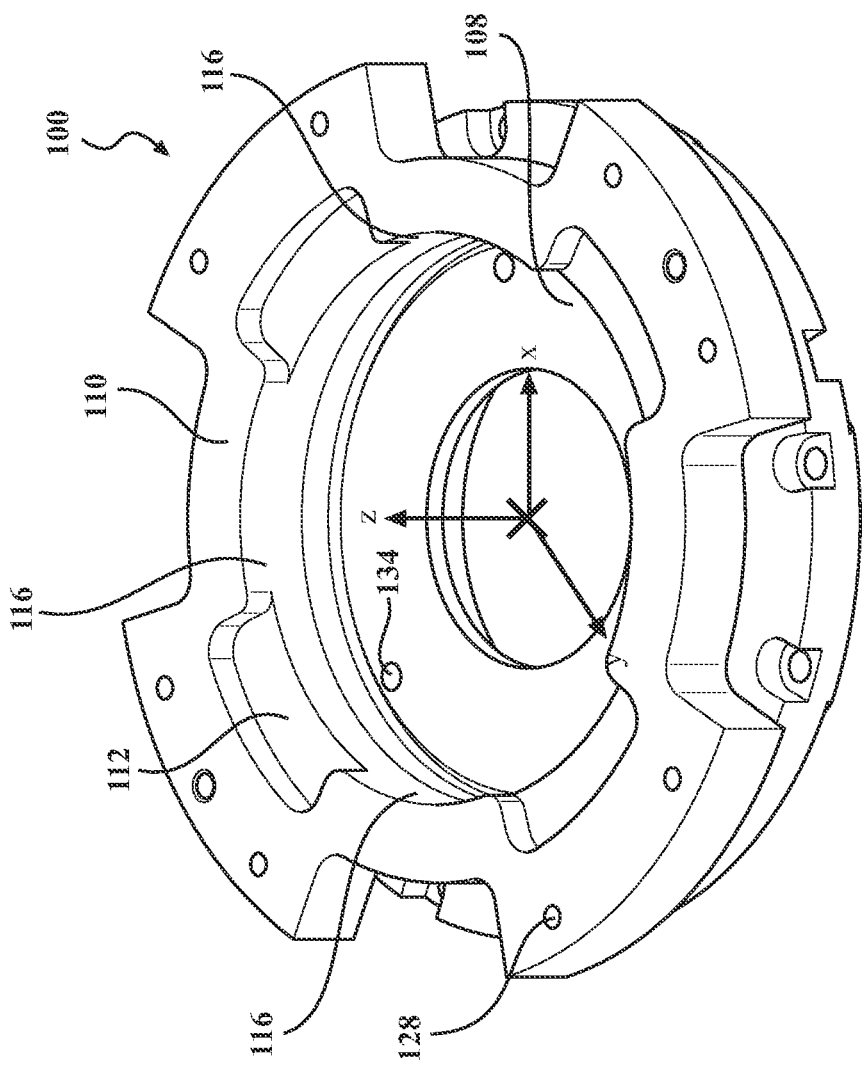

The elastic part 110 and the rigid part 108 may each include any suitable shape. Additionally, the shape of the elastic part 110 and the shape of the rigid part 108 may be independent of the shape of the body 106, as shown in FIGS. 14A and 14B. In some instances, the elastic part 110 and the rigid part 108 may include a shape to be similar to, or accommodate, a shape of a cross-section of the force/torque sensor S or the output of the transmission 33. The body 106 of the isolation mechanism 100 may include varying cross-sectional configurations for different planes relative to the z-axis. For example, the elastic part 110 may include an irregular cross-section and the rigid part 108 may include a circular cross-section. Any combination or types of cross-sectional configurations are contemplated.

Figure 17:
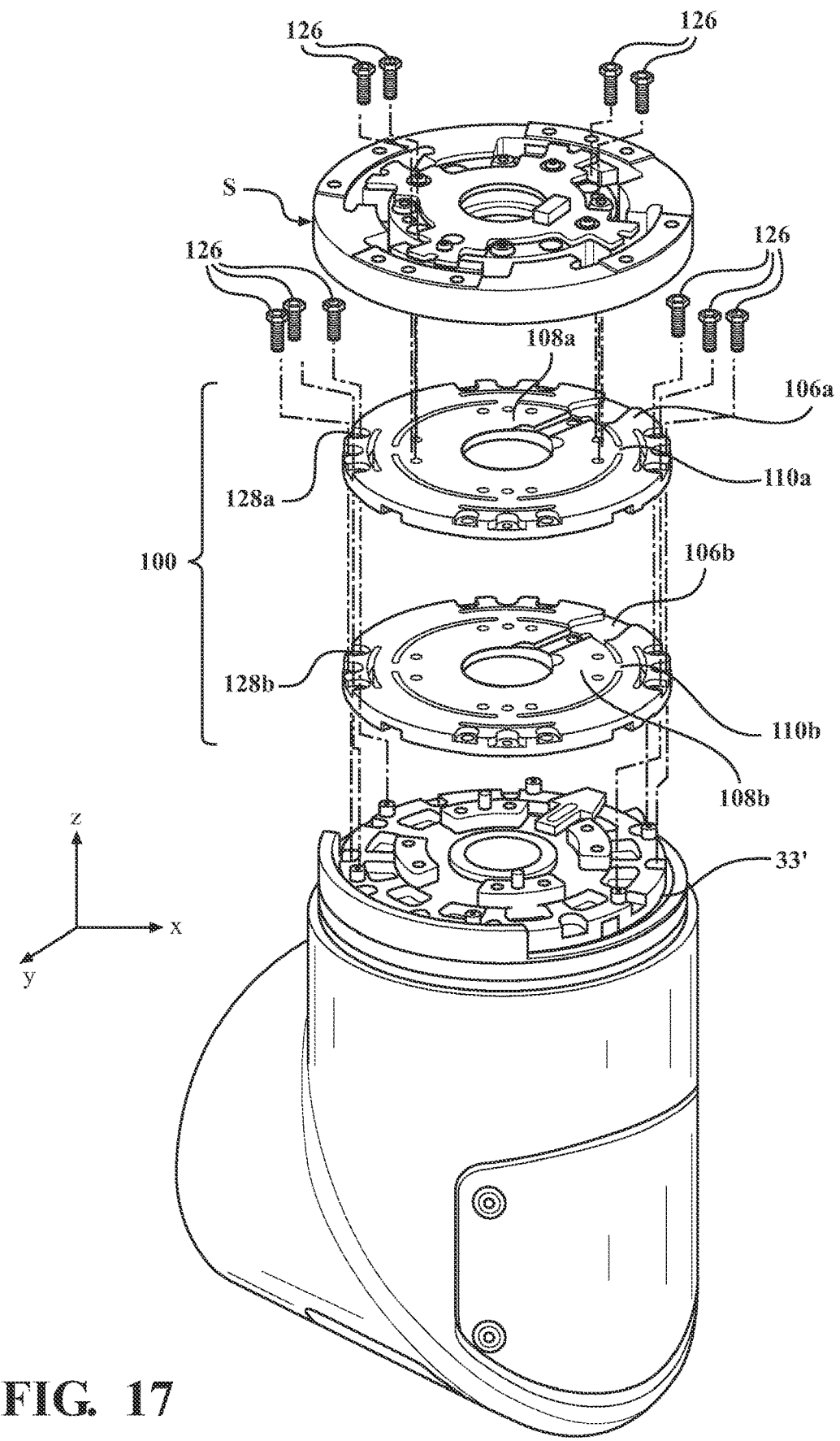
FIG. 17 is an exploded view illustrating another instance of coupling of the isolation mechanism to the force/torque sensor and the strain wave gear transmission, where the isolation mechanism includes a plurality of bodies.

In some instances, there can be multiple isolation mechanisms 100 or one isolation mechanism 100 with multiple bodies 106. For example, as shown in FIG. 17, the isolation mechanism 100 may include a first body 106a and a second body 106b. Each of the first body 106a and the second body 106b includes an elastic part 110 and a rigid part 108. As shown, the first body 106a includes a rigid part 108a and an elastic part 110a; the second body 106b includes a rigid part 108b and an elastic part 110b. The first body 106a and the second body 106b are coupled via elastic parts 110 and/or rigid parts 108. In other words, the elastic part 110a may be coupled to the elastic part 110b and/or the rigid part 108a may be coupled to the rigid part 108b. In the instance of FIG. 17, the rigid part 108a is coupled to the rigid part 108b using bolts 126 that are inserted into holes 128a of the rigid part 108a and holes 128b of the rigid part 108b. The first body 106a and the second body 106b may be coupled using any suitable method described above. As such, the isolation mechanisms 100 or bodies 106a, 106b are stacked axially along the z-axis. The isolation mechanisms 100 or bodies 106a, 106b can be disposed relative to one another axially, radially, or side by side along any of the axes.

The body 106 of the isolation mechanism can be formed of any suitable material. In one example, the body 106 comprises steel. The body 106 may alternatively comprise stainless steel. For example, the body 106 may comprise SAE Type 630 stainless steel (17-4 PH). In another example, the body 106 can be formed of custom 465 stainless steel. The body 106 can also be formed of maraging steel or iron alloy. Other steel composites, steel alloys, or plastic materials are contemplated. One skilled in the art would be able to determine the proper material to form the body 106 for the particular applications described herein.

The body 106 can also have any specified width or length. When the body 106 has a circular cross-sectional configuration, the body 106 can have any specified radius or diameter. In one example, the diameter of the body 106 is defined in a range, such as, but not limited to, between 100-300 mm, 150-250 mm or 175-225 mm Where the body 106 has cross-sectional configurations that are other than a circle (for example, an oval, rectangle or complex geometrical shape), the width and length can be defined within similar ranges. The width and length of the body 106 in one implementation is designed such that the isolation mechanism 100 can be disposed within the link assembly. One skilled in the art would be able to determine the proper dimensions for the body 106 for the particular applications described herein.

The body 106 has a predetermined thickness. The thickness can be consistent or can vary throughout the body 106. The thickness of the elastic part 110 can be the same as or different from the thickness of the rigid part 108. The thickness of the body 106 and elastic and rigid parts 110, 108 can be within a range, such as, but not limited to, a range of 2 mm-40 mm, 5 mm-20 mm, or 5 mm-10 mm. These ranges are provided as examples and one skilled in the art would be able to determine the proper thickness for the particular applications described herein.

As previously stated, the elastic part 110 of the isolation mechanism 100 is configured to deform in response to the forces induced by the transmission 33. FIGS. 18A-20C illustrate example deformations of the elastic part 110. The deformations of the elastic part 110 may be defined in relation to a central axis (z-axis) defined through a center of the body 106. In one implementation, the center is an axial center. However, the center can be a geometrical, center of gravity, centroid, or any other center.

In each of the examples throughout the figures where deformation of the isolation mechanism 100 is shown, the extent of the deformation or relative displacement may or may not be to scale. Certain aspects may be exaggerated for purposes of illustration. Deformation or relative displacement of components may or may not be visible to the naked eye while still providing the capabilities described herein.

FIGS. 18A-18E illustrate example deformations by the elastic part 110 within the plane and in a transverse direction to the z-axis. The plane is defined as the xy-plane. The axial center of the elastic part 110 is indicated using an "X". Although the z-axis is defined as the central axis defined through the center of the body 106, for the purposes of illustrating the example deformations of the elastic part 110, the z-axis should be understood as maintaining a constant position despite deformation and/or movement of the elastic part 110. An amount of deformation may be determined by comparing a distance D between the axial center of the elastic part 110 and the z-axis, where the axial center of the elastic part 110 moves a distance D during deformation. Furthermore, a direction of shifting of the elastic part 110 is indicated using an arrow.

In the examples of FIGS. 18A-18E, the isolation mechanism 100 includes the rigid part 108 and the elastic part 110. The elastic part 110 deforms and moves relative to the indicated z-axis, while the rigid part 108 remains stationary. In the examples of FIGS. 18A-18E, the elastic part 110 is disposed concentrically about the rigid part 108 such that, during deformation of the elastic part 110, the rigid part 108 is stationary and the elastic part 110 shifts about the rigid part 108. In instances where the rigid part 108 is disposed concentrically about the elastic part 110, the rigid part 108 is stationary and the elastic part 110 shifts within the rigid part 108 during deformation.

Figure 18A:
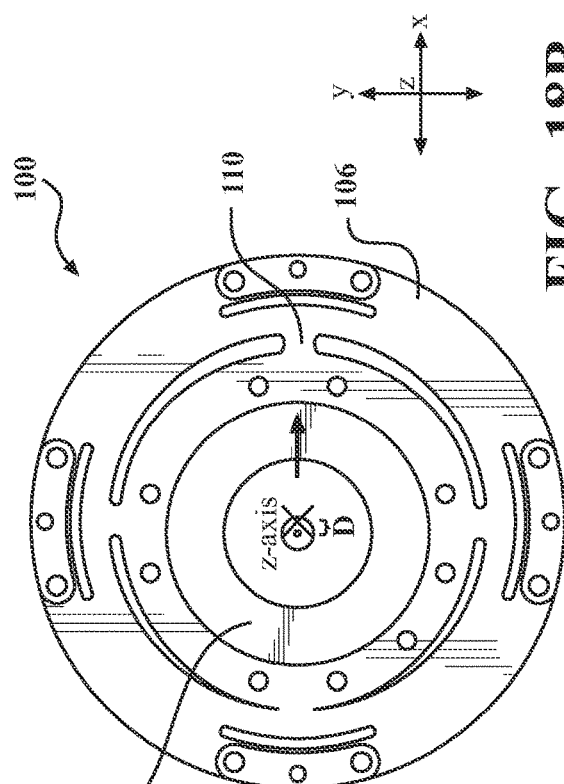
FIGS. 18A-18E are top views of one implementation of the isolation mechanism where an elastic part of the isolation mechanism deforms in a transverse direction.
Figure 18B:
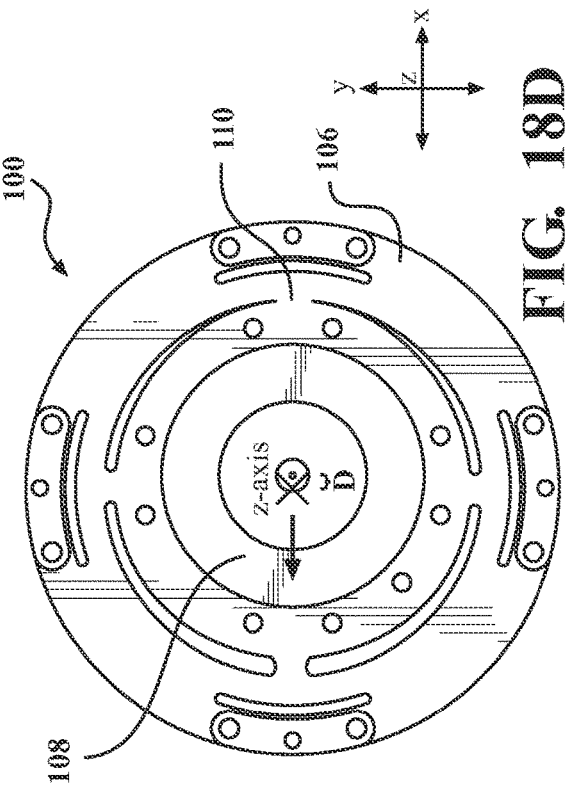
Figure 18C:
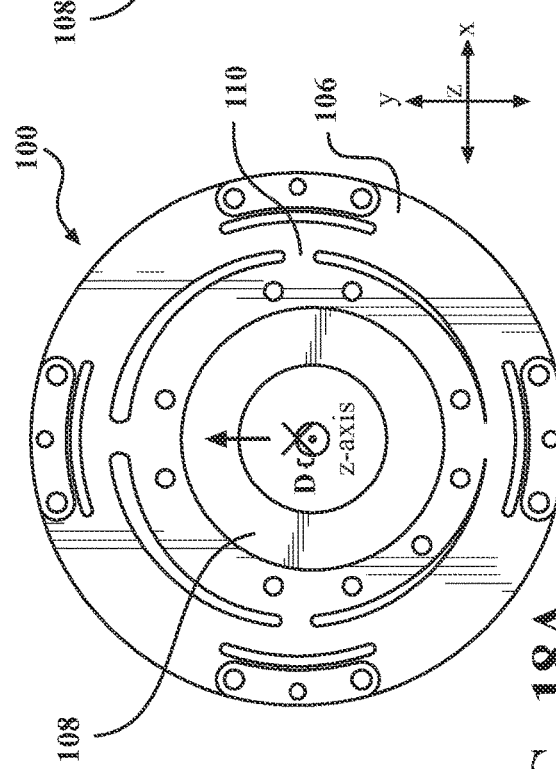
Figure 18D:
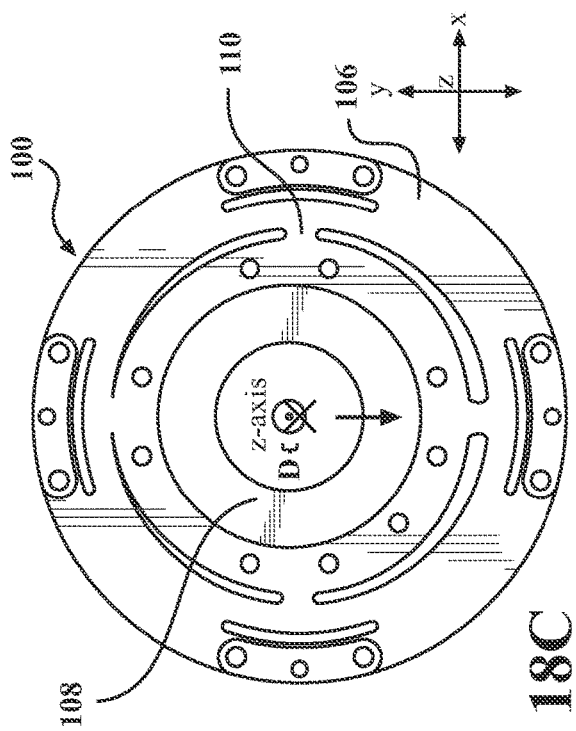

In each of FIGS. 18A-18E, the elastic part 110 deforms in a transverse direction and the axial center of the elastic part 110 rigidly shifts a distance D along the xy-plane from the z-axis. In FIG. 18A, the elastic part 110 has deformed such that the axial center of the elastic part 110 rigidly shifts a distance D in a positive y direction; in FIG. 18B, the elastic part 110 has deformed such that the axial center of the elastic part 110 rigidly shifts a distance D in a positive x direction; in FIG. 18C, the elastic part 110 has deformed such that the axial center of the elastic part 110 rigidly shifts a distance D in a negative y direction; in FIG. 18D, the elastic part 110 has deformed such that the axial center of the elastic part 110 rigidly shifts a distance D in a negative x direction; and in FIG. 18E, the elastic part 110 has deformed such that the axial center of the elastic part 110 rigidly shifts a distance D in a negative x and y direction.

Figure 19:
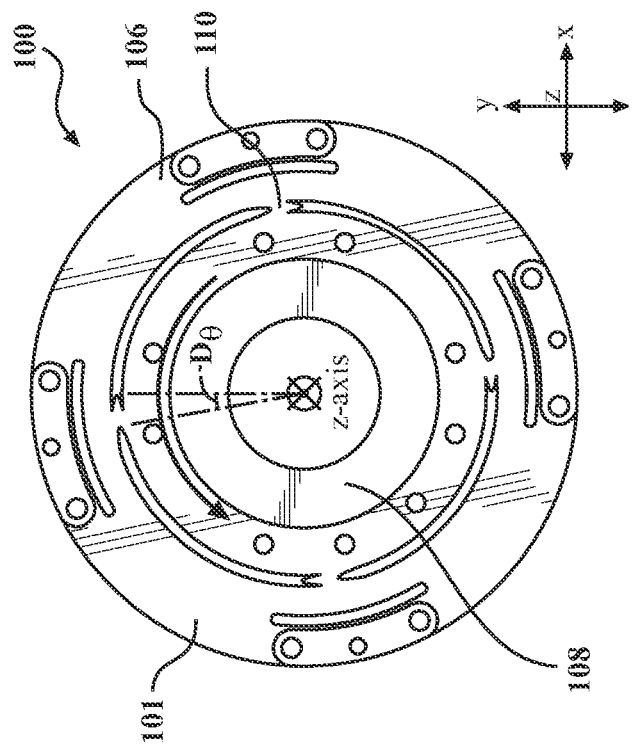
FIG. 19 is a top view of one implementation of the isolation mechanism where an elastic part of the isolation mechanism deforms in a rotational direction.
Figure 18E:
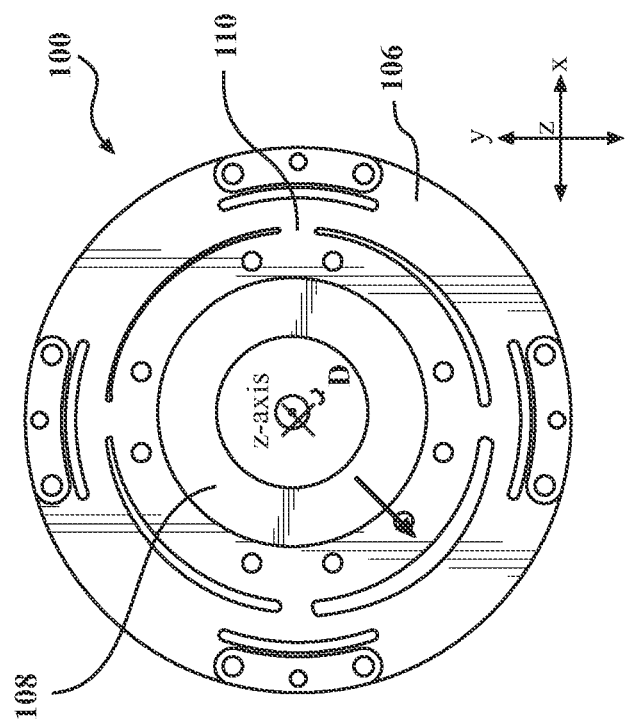

The elastic part 110 can also deform in a rotational direction about the z-axis. In FIG. 19, the elastic part 110 deforms in a rotational direction causing a rotational displacement between the rigid part 108 and the elastic part 110 by an angle Do. As such, an amount of rotational deformation may be determined by the angle Do. Furthermore, a direction of rotation of the elastic part 110 is indicated using an arrow. In this example, the rotation between the rigid part 108 and the elastic part 110 is a clockwise direction. It should be noted that, in other instances, the rotation can be in a counterclockwise direction.

The elastic part 110 of the isolation mechanism 100 is also configured to deform in an axial direction along the z-axis. FIGS. 20A-20C illustrate example deformations of the elastic part 110 in an axial direction along the z-axis. In FIGS. 20A-20C, the elastic part 110 deforms in an axial direction and shifts axially along the z-axis. Viewed alternatively, deformation of the elastic part 110 in an axial direction may cause a plane 138 of the elastic part 110 to shift along the z-axis relative to a plane 136 of the rigid part 108. As such, an amount of deformation may be determined by a distance D along the z-axis between the plane 138 of the elastic part 110 and the plane 136 of the rigid part 108. Furthermore, a direction of axial shifting of the elastic part 110 is indicated using an arrow.

In each of FIGS. 20A-20C, the elastic part 110 deforms in an axial direction relative to the z-axis such that the plane 138 of the elastic part 110 shifts a distance D along the z-axis from the plane 136 of the rigid part 108. As shown in FIG. 20A, the elastic part 110 has deformed axially relative to the z-axis, causing the plane 138 of the elastic part 110 to shift a distance D in a negative z direction. In FIG. 20B, the elastic part 110 has deformed axially along the z-axis, causing the plane 138 of the elastic part 110 to shift a distance D in a positive z direction. In FIG. 20C, the elastic part 110a and the plane 138 of the elastic part 110 have tilted axially along the z-axis, causing a first portion of the elastic part 110(1) to shift a distance D1 in a positive z direction and a second portion of the elastic part 110(2) to shift a distance D2 in a negative z direction.

In other examples, the elastic part 110 deforms in the axial direction causing a relative movement that is not planar. In other words, the elastic part 110 and/or rigid parts 108 can form a paraboloid-like (e.g., conical) or hyperbolic paraboloid-like (e.g., saddle or "potato chip") shape. In such instances, the elastic part 110 can bend or twist such that its plane section forms a hyperbola-like shape. The rigid parts 108, or relative motion therebetween, can also exhibit a similar response to accommodate such deformation. The elastic part 110 may deform in more than one of a transverse direction, a rotational direction, and an axial direction.

FIGS. 21-24 illustrate two instances where the elastic part 110 and the rigid parts 108 deforms to form a hyperbolic paraboloid-like shape. The strain wave gear transmission 33' coupled to the isolation mechanism 100 may deform during operation and exert forces on the isolation mechanism 100. For example, during operation, the strain wave gear transmission 33' may deform to a first deformation 140, shown in FIG. 21, and a second deformation 142, shown in FIG. 24.

Figure 22:
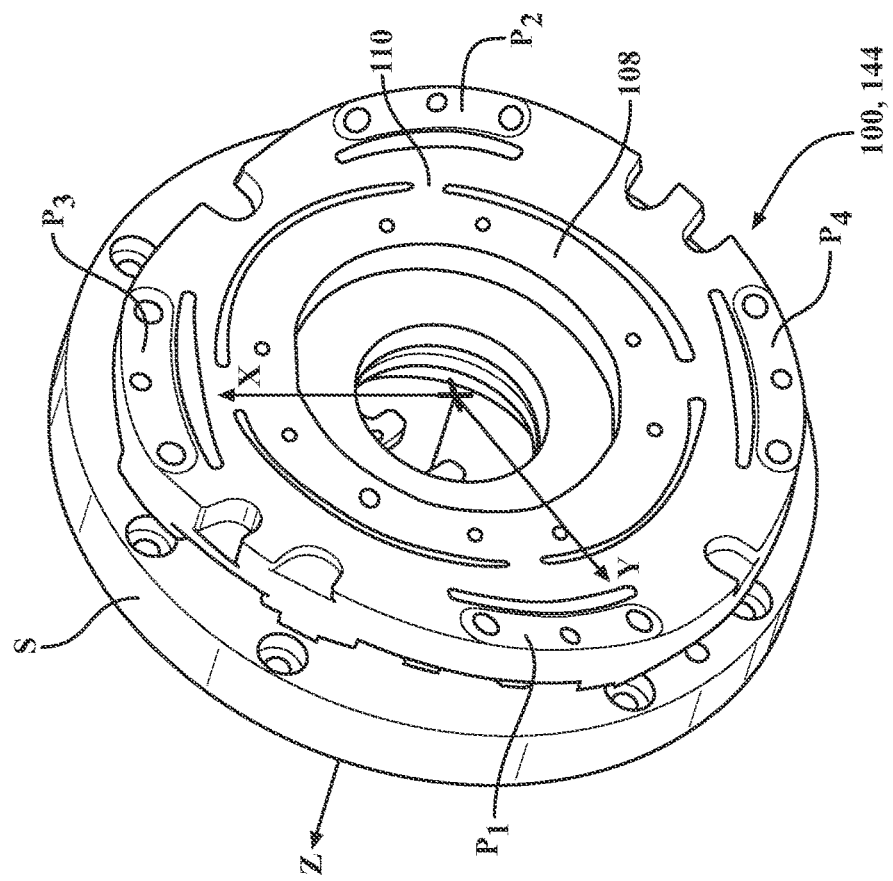
FIG. 22 is a perspective view of the isolation mechanism of FIG. 21.
Figure 21:
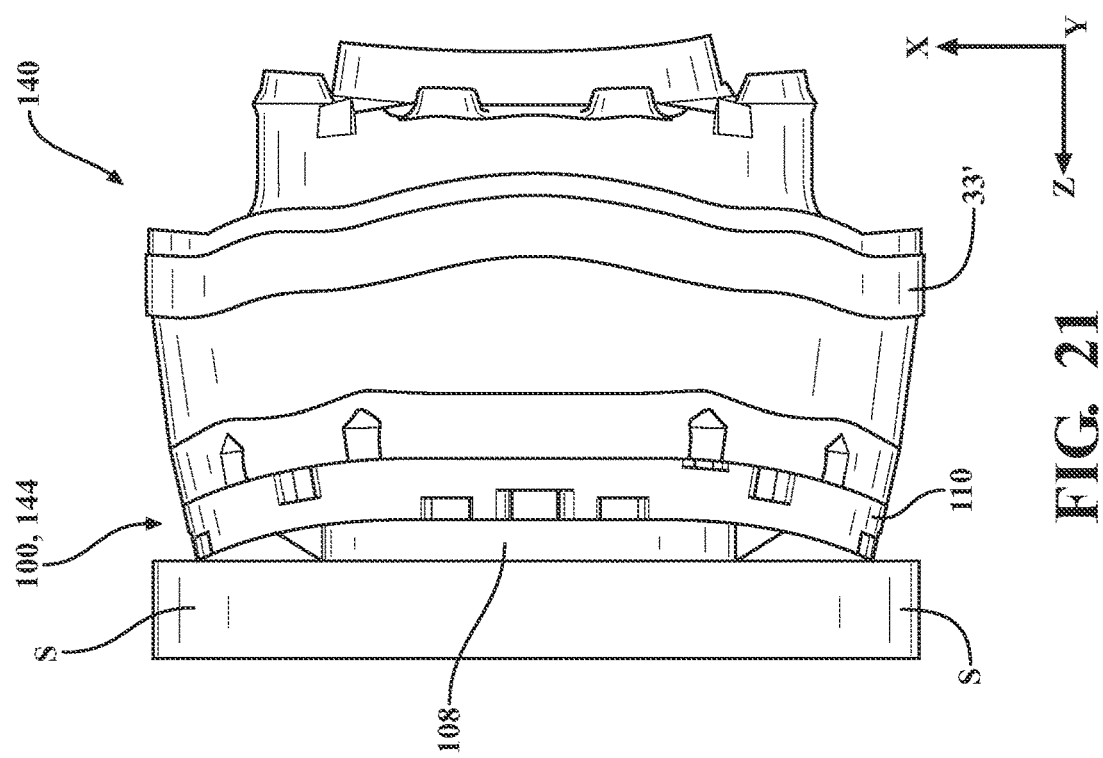
FIG. 21 is a perspective view of the force/torque sensor of FIG. 6, the strain wave gear transmission of FIG. 9A, and one implementation of the isolation mechanism where the isolation mechanism deforms to form a first hyperbolic paraboloid-like shape.

In FIG. 21, the strain wave gear transmission 33' has deformed to the first deformation 140, causing the elastic part 110 to form a first hyperbolic paraboloid-like shape 144. FIG. 22 illustrates a perspective view of the first hyperbolic paraboloid-like shape 144 of the elastic part 110 from FIG. 21. As shown in FIG. 22, the isolation mechanism 100 at points $P_1$ and $P_2$ bend toward the force/torque sensor S, and the isolation mechanism 100 at points $P_3$ and $P_4$ bend away from the force/torque sensor S. Specifically, the isolation mechanism 100 has deformed such that points $P_3$ and $P_4$ have a greater displacement along the indicated z-axis than points $P_1$ and $P_2$.

Figure 24:
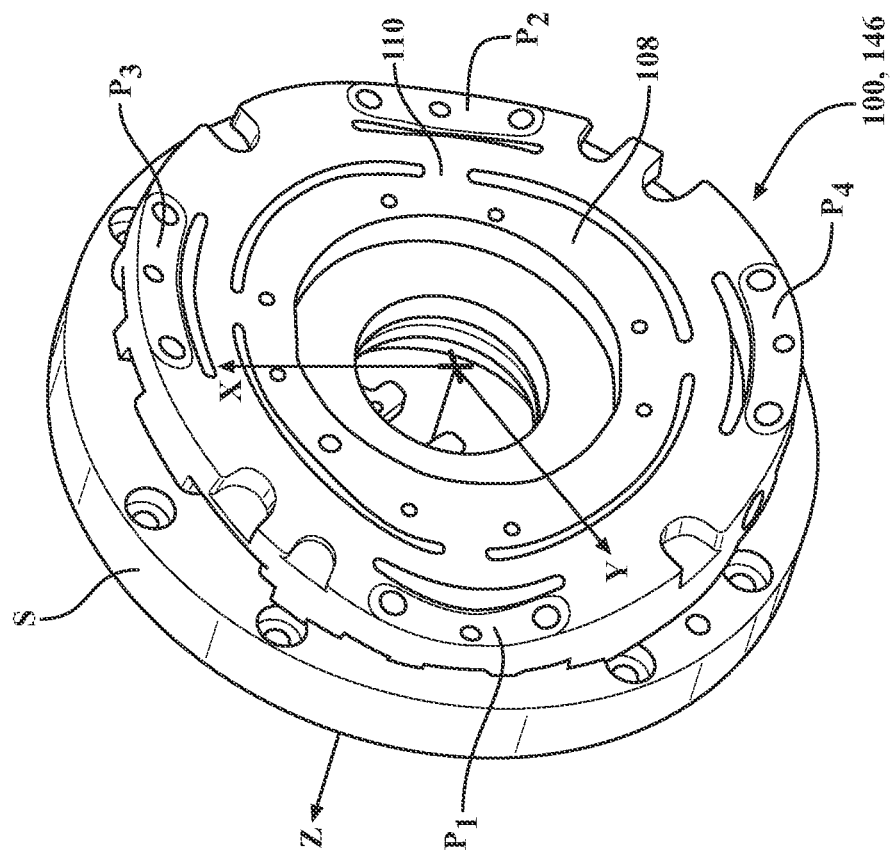
FIG. 24 is a perspective view of the isolation mechanism of FIG. 23.
Figure 23:
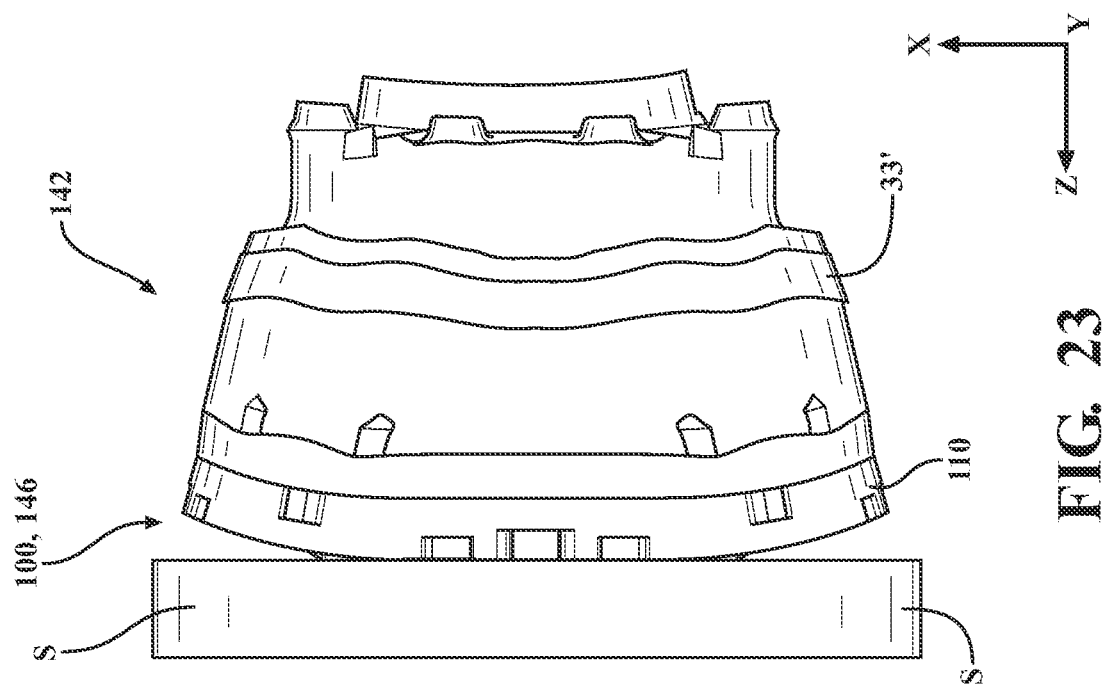
FIG. 23 is a perspective view of the force/torque sensor of FIG. 6, the strain wave gear transmission of FIG. 9A, and one implementation of the isolation mechanism where the isolation mechanism deforms to form a second hyperbolic paraboloid-like shape.

In FIG. 23, the strain wave gear transmission 33' has deformed to the second deformation 142, causing the elastic part 110 to form a second hyperbolic paraboloid-like shape 146. FIG. 24 illustrates a perspective view of the second hyperbolic paraboloid-like shape 146 of the elastic part 110 from FIG. 23. As shown in FIG. 24, the isolation mechanism 100 at points $P_1$ and $P_2$ bend away the force/torque sensor S, and the isolation mechanism 100 at points $P_3$ and $P_4$ bend toward the force/torque sensor S. Specifically, the isolation mechanism 100 has deformed such that points $P_1$ and $P_2$ have a greater displacement along the indicated z-axis than points $P_3$ and $P_4$.

While FIGS. 18A-24 illustrate instances where the elastic part 110 deforms while the rigid part 108 remains stationary, in other instances, any rigid part 108 or elastic part 110 may move in response to the elastic part 110 deforming, and the rigid part 108 or the elastic part 110 may remain stationary. For example, in some instances, the rigid part 108 may move in response to the elastic part 110 deforming. In other instances, deformation of the elastic part 110 may cause the elastic part 110 to move relative to other stationary elastic parts 110.

For example, in any of the above instances, it may be the case that the force/torque sensor S is coupled to the elastic part 110 and the transmission 33 is coupled to the rigid part 108. In such instances, the force/torque sensor S can shift in response to the elastic part 110 deforming in a transverse direction and the transmission 33 remains stationary. The skilled person understands that shifting of the force/torque sensor S to account for deformation of the elastic part 110 is negligible or designed so as to not disrupt operation of the force/torque sensor S. For example, if the elastic part 110 is coupled to the stationary part of the force/torque sensor S, the entire force/torque sensor S body can shift causing no relative displacement between the stationary and moving parts of the force/torque sensor S, and hence, no interference of readings by the force/torque sensor S. Alternatively, deformation of the elastic part 110 can be such that there is no relative displacement between a portion of the elastic part 110 coupled to the force/torque sensor S and the rigid part 108, and hence, no shifting of the force/torque sensor S. Alternatively, it may be the case that the transmission 33 is coupled to the elastic part 110 and the force/torque sensor S is coupled to the rigid part 108. In such cases, the transmission 33 can shift in response to the elastic part 110 deforming and the force/torque sensor S remains stationary. The skilled person understands that shifting of the transmission 33 to account for deformation of the elastic part 110 is negligible or designed so as to not disrupt operation of the transmission 33. Alternatively, deformation of the elastic part 110 can be such that there is no relative displacement between a portion of the elastic part 110 coupled to the force/torque sensor S and the rigid part 108, and hence, no shifting of the transmission 33.

After the isolation mechanism 100 deforms to mechanically isolate the force/torque sensor S from forces induced by the transmission 33, the elasticity of the isolation mechanism 100 causes the body 106 to immediately return to an at-rest state. As such, the isolation mechanism 100 is adapted to immediately mitigate any future forces induced by the transmission 33.

Several embodiments have been described in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. A robotic manipulator comprising:
   an arm comprising at least one joint configured to be driven by a transmission comprising an output;
   an isolation mechanism coupled to the output of the transmission; and
   a force/torque sensor comprising a body including a stationary part and a movable part coupled to and being movable relative to the stationary part, and one or more sensing elements configured to sense forces and torques applied to the movable part, wherein the force/torque sensor is coupled to the isolation mechanism; and
   wherein the isolation mechanism is configured to deform in response to forces induced by the transmission to mechanically isolate the force/torque sensor from forces induced by the transmission.

2. The robotic manipulator of claim 1, wherein the isolation mechanism comprises a body including at least one elastic part, wherein the at least one elastic part is configured to deform in response to forces induced by the transmission, and wherein the at least one elastic part is coupled to the output of the transmission.

3. The robotic manipulator of claim 2, wherein the body further includes at least one rigid part, wherein at least one rigid part is coupled to one of the stationary part and the movable part of the force/torque sensor.

4. The robotic manipulator of claim 3, wherein the at least one elastic part is disposed concentrically about the at least one rigid part.

5. The robotic manipulator of claim 3, wherein the at least one elastic part comprises a plurality of elastic segments connected to the at least one rigid part.

6. The robotic manipulator of claim 5, wherein the body of the isolation mechanism comprises a first surface and a second surface opposite the first surface, and wherein a geometrical configuration of each elastic segment is defined in part by at least two hollows formed adjacent to each elastic segment, the at least two hollows defined through the body between the first surface and the second surface.

7. The robotic manipulator of claim 3, wherein either the at least one rigid part or the at least one elastic part of the isolation mechanism is monolithically formed with the output of the transmission.

8. The robotic manipulator of claim 2, further comprising an end effector including or configured to receive a surgical instrument that includes an energy applicator, the end effector comprising an attachment mount, and wherein the robotic manipulator further comprises a distal link assembly comprising a mounting interface configured to detachably receive the attachment mount of the end effector.

9. The robotic manipulator of claim 8, wherein the force/torque sensor is disposed between the isolation mechanism and the mounting interface of the distal link assembly, wherein the movable part of the force/torque sensor is rigidly attached to the mounting interface of the distal link assembly, and wherein the force/torque sensor is configured to sense forces and/or torques applied to or experienced by the end effector or surgical instrument.

10. The robotic manipulator of claim 9, wherein the at least one elastic part of the isolation mechanism is configured to deform in response to forces induced by the transmission to mechanically isolate the force/torque sensor from forces induced by the transmission such that the force/torque sensor senses forces and/or torques applied to or experienced by the end effector or surgical instrument substantially free from interference from forces induced by the transmission.

11. The robotic manipulator of claim 9, further comprising one or more controllers configured to control the at least one joint of the arm to move the energy applicator to a commanded position, wherein the one or more controllers are configured to determine the commanded position based, in part, on the forces and/or torques applied to or experienced by the end effector or surgical instrument sensed by the force/torque sensor.

12. The robotic manipulator of claim 8, wherein the isolation mechanism is configured to support weight of the distal link assembly and the end effector.

13. The robotic manipulator of claim 2, wherein the body of the isolation mechanism comprises a planar configuration and a central axis, and an opening formed about the central axis, wherein the at least one elastic part is configured to deform within a plane perpendicular to the central axis.

14. The robotic manipulator of claim 13, wherein the at least one elastic part is configured to deform within the plane in a direction transverse to the central axis.

15. The robotic manipulator of claim 13, wherein the at least one elastic part is configured to deform within the plane in a rotational direction about the central axis.

16. The robotic manipulator of claim 13, wherein the at least one elastic part is configured to deform beyond the plane in an axial direction along the central axis.

17. The robotic manipulator of claim 13, wherein the body of the force/torque sensor comprises:
   a planar configuration and an opening aligned with the opening of the isolation mechanism; and
   a plurality of deformable members connecting the movable part and the stationary part, wherein the one or more sensing elements are disposed on the deformable members.

18. The robotic manipulator of claim 1, wherein the isolation mechanism comprises at least a first body and a second body, each comprising at least one elastic part and at least one rigid part, and wherein the at least one elastic part or the at least one rigid part of the first body is coupled to the at least one elastic part or the at least one rigid part of the second body.

19. The robotic manipulator of claim 1, wherein the transmission is further defined as a strain wave gear transmission.

20. The robotic manipulator of claim 1, wherein the isolation mechanism is absent any electrical or electronic components.

* * * * *